(12) United States Patent
Merchant et al.

(10) Patent No.: US 9,272,124 B2
(45) Date of Patent: *Mar. 1, 2016

(54) SYSTEMS AND DEVICES FOR SELECTIVE CELL LYSIS AND METHODS OF USING SAME

(71) Applicant: Ulthera, Inc., Mesa, AZ (US)

(72) Inventors: Adnan I. Merchant, Fremont, CA (US); Mark E. Deem, Mountain View, CA (US)

(73) Assignee: Ulthera, Inc., Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,375

(22) Filed: Nov. 7, 2014

(65) Prior Publication Data
US 2015/0112245 A1    Apr. 23, 2015

Related U.S. Application Data

(63) Continuation of application No. 13/799,377, filed on Mar. 13, 2013, which is a continuation of application No. 11/771,951, filed on Jun. 29, 2007, now abandoned, which is a continuation of application No.
(Continued)

(51) Int. Cl.
*G06F 17/50* (2006.01)
*G06Q 10/02* (2012.01)
*A61M 37/00* (2006.01)
(Continued)

(52) U.S. Cl.
CPC .............. *A61M 37/00* (2013.01); *A61M 5/142* (2013.01); *A61M 5/158* (2013.01); *A61M 5/165* (2013.01); *A61M 5/16827* (2013.01); *A61M 5/445* (2013.01); *G06Q 10/02* (2013.01); *G06Q 10/06* (2013.01); *A61M 2005/006* (2013.01);
(Continued)

(58) Field of Classification Search
USPC ............................... 703/5, 6, 7; 601/2; 604/24
See application file for complete search history.

(56) References Cited

U.S. PATENT DOCUMENTS 2,370,529 A    2/1945 Fuller
2,490,409 A   12/1949 Brown
(Continued)

FOREIGN PATENT DOCUMENTS

CA    1232837    2/1988
CA    1239092    7/1988
(Continued)

OTHER PUBLICATIONS

Albrecht, T., et al., Guidelines for the Use of Contrast Agents in Ultrasound, Ultraschall in Med 2004, Jan. 2004, nn. 249-256, vol. 25.
(Continued)

*Primary Examiner* — Thai Phan
(74) *Attorney, Agent, or Firm* — Knobbe Martens Olson & Bear, LLP

(57) ABSTRACT

A device for generating microbubbles in a gas and liquid mixture and injection device, the device comprising: a housing defining a mixing chamber; means for mixing solution contained in the mixing chamber to generate microbubbles in the solution; a needle array removably attached to the housing and in fluid connection with the mixing chamber, the needle array including at least one needle; and at least one pressure sensor for measuring tissue apposition pressure, the pressure sensor being mounted on one of the housing and the needle array.

20 Claims, 22 Drawing Sheets

Related U.S. Application Data

11/515,634, filed on Sep. 5, 2006, now abandoned, and a continuation-in-part of application No. 11/334,805, filed on Jan. 17, 2006, now Pat. No. 7,601,128, and a continuation-in-part of application No. 11/334,794, filed on Jan. 17, 2006, now Pat. No. 7,588,547, and a continuation-in-part of application No. 11/292,950, filed on Dec. 2, 2005, now Pat. No. 7,967,763.

(51) Int. Cl.
*G06Q 10/06* (2012.01)
*A61M 5/142* (2006.01)
*A61M 5/158* (2006.01)
*A61M 5/165* (2006.01)
*A61M 5/168* (2006.01)
*A61M 5/44* (2006.01)
*A61M 5/00* (2006.01)

(52) U.S. Cl.
CPC .................. *A61M2005/1585* (2013.01); *A61M 2005/1655* (2013.01)

(56) References Cited

U.S. PATENT DOCUMENTS

| | | |
|---|---|---|
| 2,738,172 A | 3/1956 | Spiess et al. |
| 2,945,496 A | 7/1960 | Fosdal |
| 2,961,382 A | 11/1960 | Singher et al. |
| 3,129,944 A | 4/1964 | Amos et al. |
| 3,324,854 A | 6/1967 | Weese |
| 3,590,808 A | 7/1971 | Muller |
| 3,735,336 A | 5/1973 | Long |
| 3,964,482 A | 6/1976 | Gerstel et al. |
| 3,991,763 A | 11/1976 | Genese |
| 4,150,669 A | 4/1979 | Latorre |
| 4,188,952 A | 2/1980 | Loschilov et al. |
| 4,211,949 A | 7/1980 | Brisken et al. |
| 4,212,206 A | 7/1980 | Hartemann et al. |
| 4,231,368 A | 11/1980 | Becker et al. |
| 4,248,231 A | 2/1981 | Herczog et al. |
| 4,249,923 A | 2/1981 | Walda |
| 4,276,885 A | 7/1981 | Tickner et al. |
| 4,299,219 A | 11/1981 | Norris, Jr. |
| 4,309,989 A | 1/1982 | Fahim |
| 4,373,458 A | 2/1983 | Dorosz et al. |
| 4,382,441 A | 5/1983 | Svedman |
| 4,466,442 A | 8/1984 | Hilmann et al. |
| 4,497,325 A | 2/1985 | Wedel |
| 4,536,180 A | 8/1985 | Johnson |
| 4,549,533 A | 10/1985 | Cain |
| 4,608,043 A | 8/1986 | Larkin |
| 4,641,652 A | 2/1987 | Hutterer et al. |
| 4,646,754 A | 3/1987 | Seale |
| 4,657,756 A | 4/1987 | Rasor et al. |
| 4,673,387 A | 6/1987 | Phillips et al. |
| 4,681,119 A | 7/1987 | Rasor et al. |
| 4,684,479 A | 8/1987 | D'Arrigo |
| 4,688,570 A | 8/1987 | Kramer et al. |
| 4,689,986 A | 9/1987 | Carson et al. |
| 4,718,433 A | 1/1988 | Feinstein |
| 4,720,075 A | 1/1988 | Peterson et al. |
| 4,751,921 A | 6/1988 | Park |
| 4,762,915 A | 8/1988 | Kung et al. |
| 4,774,958 A | 10/1988 | Feinstein |
| 4,796,624 A | 1/1989 | Trott et al. |
| 4,797,285 A | 1/1989 | Barenholz et al. |
| 4,815,462 A | 3/1989 | Clark |
| 4,844,080 A | 7/1989 | Frass et al. |
| 4,844,470 A | 7/1989 | Hammon et al. |
| 4,844,882 A | 7/1989 | Widder et al. |
| 4,886,491 A | 12/1989 | Parisi et al. |
| 4,900,540 A | 2/1990 | Ryan et al. |
| 4,919,986 A | 4/1990 | Lay et al. |
| 4,920,954 A | 5/1990 | Alliger et al. |
| 4,936,281 A | 6/1990 | Stasz |
| 4,936,303 A | 6/1990 | Detwiler et al. |
| 4,957,656 A | 9/1990 | Cerny et al. |
| 5,022,414 A | 6/1991 | Muller |
| 5,040,537 A | 8/1991 | Katakura |
| 5,050,537 A | 9/1991 | Fox |
| 5,069,664 A | 12/1991 | Guess et al. |
| 5,083,568 A | 1/1992 | Shimazaki et al. |
| 5,088,499 A | 2/1992 | Unger |
| 5,100,390 A | 3/1992 | Lubeck et al. |
| 5,131,600 A | 7/1992 | Klimpel |
| 5,143,063 A | 9/1992 | Fellner |
| 5,149,319 A | 9/1992 | Unger |
| 5,158,071 A | 10/1992 | Umemura et al. |
| 5,170,604 A | 12/1992 | Hedly |
| 5,178,433 A | 1/1993 | Wagner |
| 5,203,785 A | 4/1993 | Slater |
| 5,209,720 A | 5/1993 | Unger |
| 5,215,104 A | 6/1993 | Steinert |
| 5,215,680 A | 6/1993 | D'Arrigo |
| 5,216,130 A | 6/1993 | Line et al. |
| 5,219,401 A | 6/1993 | Cathignol et al. |
| 5,261,922 A | 11/1993 | Hood |
| 5,308,334 A | 5/1994 | Sancoff |
| 5,310,540 A | 5/1994 | Giddey et al. |
| 5,312,364 A | 5/1994 | Jacobs |
| 5,315,998 A | 5/1994 | Tachibana et al. |
| 5,316,000 A | 5/1994 | Chapelon et al. |
| 5,320,607 A | 6/1994 | Ishibashi |
| 5,342,380 A | 8/1994 | Hood |
| 5,352,436 A | 10/1994 | Wheatley et al. |
| 5,354,307 A | 10/1994 | Porowski |
| 5,380,411 A | 1/1995 | Schlief |
| 5,383,858 A | 1/1995 | Reilly et al. |
| 5,385,561 A | 1/1995 | Cerny |
| 5,409,126 A | 4/1995 | DeMars |
| 5,413,574 A | 5/1995 | Fugo |
| 5,415,160 A | 5/1995 | Ortiz et al. |
| 5,417,654 A | 5/1995 | Kelman |
| 5,419,761 A | 5/1995 | Narayanan et al. |
| 5,419,777 A | 5/1995 | Hofling et al. |
| 5,425,580 A | 6/1995 | Beller |
| 5,437,640 A | 8/1995 | Schwab |
| 5,441,490 A | 8/1995 | Svedman |
| 5,449,351 A | 9/1995 | Zohmann |
| 5,457,041 A | 10/1995 | Ginaven et al. |
| 5,476,368 A | 12/1995 | Rabenau et al. |
| 5,478,315 A | 12/1995 | Brothers |
| 5,494,038 A | 2/1996 | Wang et al. |
| 5,507,790 A | 4/1996 | Weiss |
| 5,522,797 A | 6/1996 | Grimm |
| 5,533,981 A | 7/1996 | Mandro et al. |
| 5,545,123 A | 8/1996 | Ortiz et al. |
| 5,556,406 A | 9/1996 | Gordon et al. |
| 5,562,693 A | 10/1996 | Devlin et al. |
| 5,569,242 A | 10/1996 | Lax et al. |
| 5,571,131 A | 11/1996 | Ek et al. |
| 5,573,002 A | 11/1996 | Pratt |
| 5,573,497 A | 11/1996 | Chapelon |
| 5,590,657 A | 1/1997 | Cain |
| 5,601,526 A | 2/1997 | Chapelon |
| 5,601,584 A | 2/1997 | Obagi et al. |
| 5,607,441 A | 3/1997 | Sierocuk et al. |
| 5,639,443 A | 6/1997 | Schutt et al. |
| 5,649,947 A | 7/1997 | Auerbach et al. |
| 5,662,646 A | 9/1997 | Fumich |
| 5,681,026 A | 10/1997 | Durand |
| 5,690,657 A | 11/1997 | Koepnick |
| 5,695,460 A | 12/1997 | Siegel et al. |
| 5,716,326 A | 2/1998 | Dannan |
| 5,733,572 A | 3/1998 | Unger et al. |
| 5,755,753 A | 5/1998 | Knowlton |
| 5,766,198 A | 6/1998 | Li |
| 5,778,894 A | 7/1998 | Dorogi et al. |
| 5,795,311 A | 8/1998 | Wess |
| 5,797,627 A | 8/1998 | Salter et al. |
| 5,817,054 A | 10/1998 | Grimm |
| 5,817,115 A | 10/1998 | Nigam |
| 5,827,204 A | 10/1998 | Grandia et al. |

(56) References Cited

U.S. PATENT DOCUMENTS

| | | |
|---|---|---|
| 5,827,216 A | 10/1998 | Igo et al. |
| 5,865,309 A | 2/1999 | Futagawa et al. |
| 5,871,524 A | 2/1999 | Knowlton |
| 5,884,631 A | 3/1999 | Silberg |
| 5,885,232 A | 3/1999 | Guitay |
| 5,902,272 A | 5/1999 | Eggers et al. |
| 5,911,700 A | 6/1999 | Mozsary et al. |
| 5,911,703 A | 6/1999 | Slate et al. |
| 5,918,757 A | 7/1999 | Przytulla et al. |
| 5,919,219 A | 7/1999 | Knowlton |
| 5,935,142 A | 8/1999 | Hood |
| 5,935,143 A | 8/1999 | Hood |
| 5,942,408 A | 8/1999 | Christensen et al. |
| 5,948,011 A | 9/1999 | Knowlton |
| 5,961,475 A | 10/1999 | Guitay |
| 5,964,776 A | 10/1999 | Peyman |
| 5,976,153 A | 11/1999 | Fischel et al. |
| 5,976,163 A | 11/1999 | Nigam |
| 5,980,517 A | 11/1999 | Gough |
| 5,983,131 A | 11/1999 | Weaver et al. |
| 5,984,915 A | 11/1999 | Loeb et al. |
| 5,993,423 A | 11/1999 | Choi |
| 5,997,501 A | 12/1999 | Gross et al. |
| 6,035,897 A | 3/2000 | Kozyuk |
| 6,039,048 A | 3/2000 | Silberg |
| 6,042,539 A | 3/2000 | Harper et al. |
| 6,047,215 A | 4/2000 | McClure et al. |
| 6,048,337 A | 4/2000 | Svedman |
| 6,066,131 A | 5/2000 | Mueller et al. |
| 6,071,239 A | 6/2000 | Cribbs et al. |
| 6,083,236 A | 7/2000 | Feingold |
| 6,102,887 A | 8/2000 | Altman |
| 6,113,558 A | 9/2000 | Rosenschein et al. |
| 6,117,152 A | 9/2000 | Huitema |
| RE36,939 E | 10/2000 | Tachibana et al. |
| 6,128,958 A | 10/2000 | Cain |
| 6,132,755 A | 10/2000 | Eicher et al. |
| 6,139,518 A | 10/2000 | Mozsary et al. |
| 6,155,989 A | 12/2000 | Collins |
| 6,162,232 A | 12/2000 | Shadduck |
| 6,176,854 B1 | 1/2001 | Cone |
| 6,183,442 B1 | 2/2001 | Athanasiou et al. |
| 6,193,672 B1 | 2/2001 | Clement |
| 6,200,291 B1 | 3/2001 | Di Pietro |
| 6,200,313 B1 | 3/2001 | Abe et al. |
| 6,203,540 B1 | 3/2001 | Weber et al. |
| 6,210,393 B1 | 4/2001 | Brisken |
| 6,237,604 B1 | 5/2001 | Burnside et al. |
| 6,241,753 B1 | 6/2001 | Knowlten |
| 6,254,580 B1 | 7/2001 | Svedman |
| 6,254,614 B1 | 7/2001 | Jesseph |
| 6,258,056 B1 | 7/2001 | Turley et al. |
| 6,258,378 B1 | 7/2001 | Schneider et al. |
| 6,261,272 B1 | 7/2001 | Gross et al. |
| 6,273,877 B1 | 8/2001 | West et al. |
| 6,277,116 B1 | 8/2001 | Utely et al. |
| 6,280,401 B1 | 8/2001 | Mahurkar |
| 6,302,863 B1 | 10/2001 | Tankovich |
| 6,309,355 B1 | 10/2001 | Cain et al. |
| 6,311,090 B1 | 10/2001 | Knowlton |
| 6,312,439 B1 | 11/2001 | Gordon |
| 6,315,756 B1 | 11/2001 | Tankovich |
| 6,315,777 B1 | 11/2001 | Comben |
| 6,319,230 B1 | 11/2001 | Palasis et al. |
| 6,321,109 B2 | 11/2001 | Ben-Haim et al. |
| 6,325,801 B1 | 12/2001 | Monnier |
| 6,338,710 B1 | 1/2002 | Takahashi et al. |
| 6,350,276 B1 | 2/2002 | Knowlton |
| 6,366,206 B1 | 4/2002 | Ishikawa |
| 6,375,634 B1 | 4/2002 | Carroll |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,391,020 B1 | 5/2002 | Kurtz et al. |
| 6,391,023 B1 | 5/2002 | Weber et al. |
| 6,397,098 B1 | 5/2002 | Uber, III et al. |
| 6,405,090 B1 | 6/2002 | Knowlton |
| 6,409,665 B1 | 6/2002 | Scott et al. |
| 6,413,216 B1 | 7/2002 | Cain et al. |
| 6,413,255 B1 | 7/2002 | Stern |
| 6,425,912 B1 | 7/2002 | Knowlton |
| 6,430,446 B1 | 8/2002 | Knowlton |
| 6,432,101 B1 | 8/2002 | Weber et al. |
| 6,436,078 B1 | 8/2002 | Svedman |
| 6,438,424 B1 | 8/2002 | Knowlton |
| 6,440,096 B1 | 8/2002 | Lastovich et al. |
| 6,440,121 B1 | 8/2002 | Weber et al. |
| 6,443,914 B1 | 9/2002 | Costantino |
| 6,450,979 B1 | 9/2002 | Miwa |
| 6,451,240 B1 | 9/2002 | Sherman et al. |
| 6,453,202 B1 | 9/2002 | Knowlton |
| 6,454,730 B1 | 9/2002 | Hechel et al. |
| 6,461,350 B1 | 10/2002 | Underwood et al. |
| 6,461,378 B1 | 10/2002 | Knowlton |
| 6,464,680 B1 | 10/2002 | Brisken et al. |
| 6,470,216 B1 | 10/2002 | Knowlton |
| 6,470,218 B1 | 10/2002 | Behl |
| 6,479,034 B1 | 11/2002 | Unger et al. |
| 6,500,141 B1 | 12/2002 | Irion et al. |
| 6,506,611 B2 | 1/2003 | Bienert et al. |
| 6,511,463 B1 | 1/2003 | Wood et al. |
| 6,514,220 B2 | 2/2003 | Melton |
| 6,517,498 B1 | 2/2003 | Burbank et al. |
| 6,537,242 B1 | 3/2003 | Palmer |
| 6,537,246 B1 | 3/2003 | Unger et al. |
| 6,544,201 B1 | 4/2003 | Guitay |
| 6,569,176 B2 | 5/2003 | Jesseph |
| 6,572,839 B2 | 6/2003 | Sugita |
| 6,575,930 B1 | 6/2003 | Trombley, III et al. |
| 6,582,442 B2 | 6/2003 | Simon et al. |
| 6,585,678 B1 | 7/2003 | Tachibana et al. |
| 6,599,305 B1 | 7/2003 | Feingold |
| 6,602,251 B2 | 8/2003 | Burbank et al. |
| 6,605,079 B2 | 8/2003 | Shanks et al. |
| 6,605,080 B1 | 8/2003 | Altshuler et al. |
| 6,607,498 B2 | 8/2003 | Eshel |
| 6,611,707 B1 | 8/2003 | Prausnitz et al. |
| 6,615,166 B1 | 9/2003 | Guheen et al. |
| 6,623,457 B1 | 9/2003 | Rosenberg |
| 6,626,854 B2 | 9/2003 | Friedman et al. |
| 6,629,949 B1 | 10/2003 | Douglas |
| 6,638,767 B2 | 10/2003 | Unger et al. |
| 6,645,162 B2 | 11/2003 | Friedman et al. |
| 6,662,054 B2 | 12/2003 | Kreindel et al. |
| 6,663,616 B1 | 12/2003 | Roth et al. |
| 6,663,618 B2 | 12/2003 | Weber et al. |
| 6,663,820 B2 | 12/2003 | Arias et al. |
| 6,685,657 B2 | 2/2004 | Jones |
| 6,687,537 B2 | 2/2004 | Bernabei |
| 6,695,781 B2 | 2/2004 | Rabiner |
| 6,695,808 B2 | 2/2004 | Tom |
| 6,702,779 B2 | 3/2004 | Connelly et al. |
| 6,725,095 B2 | 4/2004 | Fenn et al. |
| 6,730,061 B1 | 5/2004 | Cuschieri et al. |
| 6,743,211 B1 | 6/2004 | Prausnitz et al. |
| 6,743,215 B2 | 6/2004 | Bernabei |
| 6,749,624 B2 | 6/2004 | Knowlton |
| 6,770,071 B2 | 8/2004 | Woloszko et al. |
| 6,780,171 B2 | 8/2004 | Gabel et al. |
| 6,795,727 B2 | 9/2004 | Giammarusti |
| 6,795,728 B2 | 9/2004 | Chornenky et al. |
| 6,817,988 B2 | 11/2004 | Bergeron et al. |
| 6,826,429 B2 | 11/2004 | Johnson et al. |
| 6,855,133 B2 | 2/2005 | Svedman |
| 6,882,884 B1 | 4/2005 | Mosk et al. |
| 6,883,729 B2 | 4/2005 | Putvinski et al. |
| 6,889,090 B2 | 5/2005 | Kreindel |
| 6,892,099 B2 | 5/2005 | Jaafar et al. |
| 6,896,659 B2 | 5/2005 | Conston et al. |
| 6,896,666 B2 | 5/2005 | Kochamba |
| 6,896,674 B1 | 5/2005 | Woloszko et al. |
| 6,902,554 B2 | 6/2005 | Huttner |

(56) References Cited

U.S. PATENT DOCUMENTS

| | | |
|---|---|---|
| 6,905,480 B2 | 6/2005 | McGuckin et al. |
| 6,910,671 B1 | 6/2005 | Korkus et al. |
| 6,916,328 B2 | 7/2005 | Brett et al. |
| 6,918,907 B2 | 7/2005 | Kelly et al. |
| 6,918,908 B2 | 7/2005 | Bonner et al. |
| 6,920,883 B2 | 7/2005 | Bessette et al. |
| 6,926,683 B1 | 8/2005 | Kochman et al. |
| 6,931,277 B1 | 8/2005 | Yuzhakov et al. |
| 6,945,937 B2 | 9/2005 | Culp et al. |
| 6,957,186 B1 | 10/2005 | Guheen et al. |
| 6,960,205 B2 | 11/2005 | Jahns et al. |
| 6,971,994 B1 | 12/2005 | Young |
| 6,974,450 B2 | 12/2005 | Weber |
| 6,994,691 B2 | 2/2006 | Ejlersen |
| 6,994,705 B2 | 2/2006 | Nebis et al. |
| 7,066,922 B2 | 6/2006 | Angel et al. |
| 7,083,580 B2 | 8/2006 | Bernabei |
| 7,115,108 B2 | 10/2006 | Wilkinson et al. |
| 7,149,698 B2 | 12/2006 | Guheen et al. |
| 7,153,306 B2 | 12/2006 | Ralph et al. |
| 7,169,115 B2 | 1/2007 | Nobis et al. |
| 7,184,614 B2 | 2/2007 | Slatkine |
| 7,184,826 B2 | 2/2007 | Cormier et al. |
| 7,186,252 B2 | 3/2007 | Nobis et al. |
| 7,217,265 B2 | 5/2007 | Hennings et al. |
| 7,223,275 B2 | 5/2007 | Shiuey |
| 7,226,446 B1 | 6/2007 | Mody et al. |
| 7,238,183 B2 | 7/2007 | Kreindel |
| 7,250,047 B2 | 7/2007 | Anderson et al. |
| 7,252,641 B2 | 8/2007 | Thompson et al. |
| 7,258,674 B2 | 8/2007 | Cribbs et al. |
| 7,278,991 B2 | 10/2007 | Morris et al. |
| 7,306,095 B1 | 12/2007 | Bourque et al. |
| 7,315,826 B1 | 1/2008 | Guheen et al. |
| 7,331,951 B2 | 2/2008 | Eshel et al. |
| 7,335,158 B2 | 2/2008 | Taylor |
| 7,338,551 B2 | 3/2008 | Kozyuk |
| 7,347,855 B2 | 3/2008 | Eshel et al. |
| 7,351,295 B2 | 4/2008 | Pawlik et al. |
| 7,374,551 B2 | 5/2008 | Liang |
| 7,376,460 B2 | 5/2008 | Bernabei |
| 7,392,080 B2 | 6/2008 | Eppstein et al. |
| 7,410,476 B2 | 8/2008 | Wilkinson et al. |
| 7,419,798 B2 | 9/2008 | Ericson |
| 7,437,189 B2 | 10/2008 | Matsumura et al. |
| 7,442,192 B2 | 10/2008 | Knowlton |
| 7,452,358 B2 | 11/2008 | Stern et al. |
| 7,455,663 B2 | 11/2008 | Bikovsky |
| 7,470,237 B2 | 12/2008 | Beckman et al. |
| 7,473,251 B2 | 1/2009 | Knowlton et al. |
| 7,479,104 B2 | 1/2009 | Lau et al. |
| 7,494,488 B2 | 2/2009 | Weber |
| 7,507,209 B2 | 3/2009 | Nezhat et al. |
| 7,524,318 B2 | 4/2009 | Young et al. |
| 7,546,918 B2 | 6/2009 | Gollier et al. |
| 7,559,905 B2 | 7/2009 | Kagosaki et al. |
| 7,566,318 B2 | 7/2009 | Haefner |
| 7,585,281 B2 | 9/2009 | Nezhat et al. |
| 7,588,547 B2 * | 9/2009 | Deem et al. ........................ 601/2 |
| 7,588,557 B2 | 9/2009 | Nakao |
| 7,601,128 B2 * | 10/2009 | Deem et al. ........................ 601/2 |
| 7,625,354 B2 | 12/2009 | Hochman |
| 7,625,371 B2 | 12/2009 | Morris et al. |
| 7,678,097 B1 | 3/2010 | Peluso et al. |
| 7,740,600 B2 | 6/2010 | Slatkine et al. |
| 7,762,964 B2 | 7/2010 | Slatkine et al. |
| 7,762,965 B2 | 7/2010 | Slatkine et al. |
| 7,770,611 B2 | 8/2010 | Houwaert et al. |
| 7,771,374 B2 | 8/2010 | Slatkine et al. |
| 7,824,348 B2 | 11/2010 | Barthe et al. |
| 7,828,827 B2 | 11/2010 | Gartstein et al. |
| 7,842,008 B2 | 11/2010 | Clarke et al. |
| 7,901,421 B2 | 3/2011 | Shiuey et al. |
| 7,935,139 B2 | 5/2011 | Slatkine et al. |
| 7,938,824 B2 | 5/2011 | Chornenky et al. |
| 7,967,763 B2 * | 6/2011 | Deem et al. ........................ 601/2 |
| 7,985,199 B2 | 7/2011 | Kornerup et al. |
| 8,025,658 B2 | 9/2011 | Chong et al. |
| 8,083,715 B2 | 12/2011 | Sonoda et al. |
| 8,086,322 B2 | 12/2011 | Schouenborg |
| 8,103,355 B2 | 1/2012 | Mulholland et al. |
| 8,127,771 B2 | 3/2012 | Hennings |
| 8,133,191 B2 | 3/2012 | Rosenberg et al. |
| 8,256,429 B2 | 9/2012 | Hennings et al. |
| 8,348,867 B2 * | 1/2013 | Deem ................ A61K 41/0028 600/2 |
| 8,357,146 B2 | 1/2013 | Hennings et al. |
| 8,366,643 B2 * | 2/2013 | Deem ................ A61K 41/0028 600/439 |
| 8,401,668 B2 | 3/2013 | Deem et al. |
| 8,406,894 B2 * | 3/2013 | Johnson ................ A61N 5/04 606/33 |
| 8,439,940 B2 | 5/2013 | Chomas et al. |
| 8,518,069 B2 | 8/2013 | Clark, III et al. |
| 8,535,302 B2 | 9/2013 | Ben-Haim et al. |
| 8,540,705 B2 | 9/2013 | Mehta |
| 8,573,227 B2 | 11/2013 | Hennings et al. |
| 8,608,737 B2 | 12/2013 | Mehta et al. |
| 8,636,665 B2 | 1/2014 | Slayton et al. |
| 8,652,123 B2 | 2/2014 | Gurtner et al. |
| 8,663,112 B2 | 3/2014 | Slayton et al. |
| 8,671,622 B2 | 3/2014 | Thomas |
| 8,672,848 B2 | 3/2014 | Slayton et al. |
| 8,676,338 B2 | 3/2014 | Levinson |
| 8,685,012 B2 | 4/2014 | Hennings et al. |
| 8,753,339 B2 | 6/2014 | Clark, III et al. |
| 8,771,263 B2 | 7/2014 | Epshtein et al. |
| 8,825,176 B2 | 9/2014 | Johnson et al. |
| 8,834,547 B2 | 9/2014 | Anderson et al. |
| 8,868,204 B2 | 10/2014 | Edoute et al. |
| 8,882,753 B2 | 11/2014 | Mehta et al. |
| 8,882,758 B2 | 11/2014 | Nebrigie et al. |
| 8,894,678 B2 | 11/2014 | Clark, III et al. |
| 8,900,261 B2 | 12/2014 | Clark, III et al. |
| 8,900,262 B2 | 12/2014 | Clark, III et al. |
| 8,979,882 B2 | 3/2015 | Drews et al. |
| 2001/0001829 A1 | 5/2001 | Sugimura et al. |
| 2001/0004702 A1 | 6/2001 | Peyman |
| 2001/0014805 A1 | 8/2001 | Burbank et al. |
| 2001/0053887 A1 | 12/2001 | Douglas et al. |
| 2002/0029053 A1 | 3/2002 | Gordon |
| 2002/0082528 A1 | 6/2002 | Friedman et al. |
| 2002/0082589 A1 | 6/2002 | Friedman et al. |
| 2002/0099356 A1 | 7/2002 | Unger et al. |
| 2002/0111569 A1 | 8/2002 | Rosenschein |
| 2002/0120238 A1 | 8/2002 | McGuckin et al. |
| 2002/0120260 A1 | 8/2002 | Morris et al. |
| 2002/0120261 A1 | 8/2002 | Morris et al. |
| 2002/0130126 A1 | 9/2002 | Rosenberg |
| 2002/0134733 A1 | 9/2002 | Kerfoot |
| 2002/0137991 A1 | 9/2002 | Scarantino |
| 2002/0169394 A1 | 11/2002 | Eppstein et al. |
| 2002/0177846 A1 | 11/2002 | Mulier |
| 2002/0185557 A1 | 12/2002 | Sparks |
| 2002/0193784 A1 | 12/2002 | McHale et al. |
| 2002/0193831 A1 | 12/2002 | Smith, III |
| 2003/0006677 A1 | 1/2003 | Okuda et al. |
| 2003/0009153 A1 | 1/2003 | Brisken et al. |
| 2003/0069502 A1 | 4/2003 | Makin et al. |
| 2003/0074023 A1 | 4/2003 | Kaplan et al. |
| 2003/0083536 A1 | 5/2003 | Eshel et al. |
| 2003/0120269 A1 | 6/2003 | Bessette et al. |
| 2003/0130628 A1 | 7/2003 | Duffy |
| 2003/0130655 A1 | 7/2003 | Woloszko et al. |
| 2003/0130711 A1 | 7/2003 | Pearson et al. |
| 2003/0139740 A1 | 7/2003 | Kreindel |
| 2003/0139755 A1 | 7/2003 | Dybbs |
| 2003/0153905 A1 | 8/2003 | Edwards et al. |
| 2003/0153960 A1 | 8/2003 | Chornenky et al. |
| 2003/0171670 A1 | 9/2003 | Gumb et al. |
| 2003/0187371 A1 | 10/2003 | Vortman et al. |
| 2003/0212350 A1 | 11/2003 | Tadlock |
| 2003/0228254 A1 | 12/2003 | Klaveness et al. |
| 2003/0233083 A1 | 12/2003 | Houwaert |

(56) References Cited

U.S. PATENT DOCUMENTS

| | | |
|---|---|---|
| 2003/0233110 A1 | 12/2003 | Jesseph |
| 2004/0006566 A1 | 1/2004 | Taylor et al. |
| 2004/0019299 A1 | 1/2004 | Ritchart et al. |
| 2004/0019371 A1 | 1/2004 | Jaafar et al. |
| 2004/0023844 A1 | 2/2004 | Pettis et al. |
| 2004/0030263 A1 | 2/2004 | Dubrul et al. |
| 2004/0039312 A1 | 2/2004 | Hillstead et al. |
| 2004/0058882 A1 | 3/2004 | Eriksson et al. |
| 2004/0073144 A1 | 4/2004 | Carava |
| 2004/0073206 A1 | 4/2004 | Foley et al. |
| 2004/0079371 A1 | 4/2004 | Gray |
| 2004/0097967 A1 | 5/2004 | Ignon |
| 2004/0106867 A1 | 6/2004 | Eshel et al. |
| 2004/0120861 A1 | 6/2004 | Petroff |
| 2004/0122483 A1 | 6/2004 | Nathan et al. |
| 2004/0138712 A1 | 7/2004 | Tamarkin et al. |
| 2004/0158150 A1 | 8/2004 | Rabiner |
| 2004/0162546 A1 | 8/2004 | Liang et al. |
| 2004/0162554 A1 | 8/2004 | Lee et al. |
| 2004/0167558 A1 | 8/2004 | Igo et al. |
| 2004/0186425 A1 | 9/2004 | Schneider et al. |
| 2004/0200909 A1 | 10/2004 | McMillan et al. |
| 2004/0202576 A1 | 10/2004 | Aceti et al. |
| 2004/0206365 A1 | 10/2004 | Knowlton |
| 2004/0210214 A1 | 10/2004 | Knowlton |
| 2004/0215101 A1 | 10/2004 | Rioux et al. |
| 2004/0215110 A1 | 10/2004 | Kreindel |
| 2004/0220512 A1 | 11/2004 | Kreindel |
| 2004/0236248 A1 | 11/2004 | Svedman |
| 2004/0236252 A1 | 11/2004 | Muzzi et al. |
| 2004/0243159 A1 | 12/2004 | Shiuey |
| 2004/0243160 A1 | 12/2004 | Shiuey et al. |
| 2004/0251566 A1 | 12/2004 | Kozyuk |
| 2004/0253148 A1 | 12/2004 | Leaton |
| 2004/0253183 A1 | 12/2004 | Uber, III et al. |
| 2004/0264293 A1 | 12/2004 | Laugharn et al. |
| 2005/0010197 A1 | 1/2005 | Lau et al. |
| 2005/0015024 A1 | 1/2005 | Babaev |
| 2005/0027242 A1 | 2/2005 | Gabel et al. |
| 2005/0033338 A1 | 2/2005 | Ferree |
| 2005/0049543 A1 | 3/2005 | Anderson et al. |
| 2005/0055018 A1 | 3/2005 | Kreindel |
| 2005/0080333 A1 | 4/2005 | Piron et al. |
| 2005/0085748 A1 | 4/2005 | Culp et al. |
| 2005/0102009 A1 | 5/2005 | Costantino |
| 2005/0131439 A1 | 6/2005 | Brett et al. |
| 2005/0136548 A1 | 6/2005 | McDevitt |
| 2005/0137525 A1 | 6/2005 | Wang et al. |
| 2005/0139142 A1 | 6/2005 | Kelley et al. |
| 2005/0154309 A1 | 7/2005 | Etchells et al. |
| 2005/0154314 A1 | 7/2005 | Quistgaard |
| 2005/0154443 A1 | 7/2005 | Linder et al. |
| 2005/0163711 A1 | 7/2005 | Nycz et al. |
| 2005/0182385 A1 | 8/2005 | Epley |
| 2005/0182462 A1 | 8/2005 | Chornenky et al. |
| 2005/0191252 A1 | 9/2005 | Mutsui |
| 2005/0203497 A1 | 9/2005 | Speeg |
| 2005/0215987 A1 | 9/2005 | Slatkine |
| 2005/0234527 A1 | 10/2005 | Slatkine |
| 2005/0256536 A1 | 11/2005 | Grundeman et al. |
| 2005/0268703 A1 | 12/2005 | Funck et al. |
| 2006/0036300 A1 | 2/2006 | Kreindel |
| 2006/0058678 A1 | 3/2006 | Vitek et al. |
| 2006/0074313 A1 | 4/2006 | Slayton |
| 2006/0074314 A1 | 4/2006 | Slayton et al. |
| 2006/0079921 A1 | 4/2006 | Nezhat et al. |
| 2006/0094988 A1 | 5/2006 | Tosaya et al. |
| 2006/0100555 A1 | 5/2006 | Cagle et al. |
| 2006/0111744 A1 | 5/2006 | Makin et al. |
| 2006/0122509 A1 | 6/2006 | Desilets |
| 2006/0206040 A1 | 9/2006 | Greenberg |
| 2006/0206117 A1 | 9/2006 | Harp |
| 2006/0211958 A1 | 9/2006 | Rosenberg et al. |
| 2006/0235732 A1 | 10/2006 | Miller et al. |
| 2006/0241672 A1 | 10/2006 | Zadini et al. |
| 2006/0241673 A1 | 10/2006 | Zadini |
| 2006/0259102 A1 | 11/2006 | Slatkine |
| 2006/0264809 A1 | 11/2006 | Hansmann et al. |
| 2006/0264926 A1 | 11/2006 | Kochamba |
| 2006/0293722 A1 | 12/2006 | Slatkine et al. |
| 2007/0005091 A1 | 1/2007 | Zadini et al. |
| 2007/0010810 A1 | 1/2007 | Kochamba |
| 2007/0016234 A1 | 1/2007 | Daxer |
| 2007/0027411 A1 | 2/2007 | Ella et al. |
| 2007/0031482 A1 | 2/2007 | Castro et al. |
| 2007/0035201 A1 | 2/2007 | Desilets et al. |
| 2007/0041961 A1 | 2/2007 | Hwang et al. |
| 2007/0043295 A1 | 2/2007 | Chomas et al. |
| 2007/0055156 A1 | 3/2007 | Desilets et al. |
| 2007/0055179 A1 | 3/2007 | Deem et al. |
| 2007/0060989 A1 | 3/2007 | Deem et al. |
| 2007/0118077 A1 | 5/2007 | Clarke et al. |
| 2007/0118166 A1 | 5/2007 | Nobis et al. |
| 2007/0129708 A1 | 6/2007 | Edwards et al. |
| 2007/0142881 A1 | 6/2007 | Hennings |
| 2007/0156096 A1 | 7/2007 | Sonoda et al. |
| 2007/0179515 A1 | 8/2007 | Matsutani et al. |
| 2007/0191827 A1 | 8/2007 | Lischinsky et al. |
| 2007/0197907 A1 | 8/2007 | Bruder et al. |
| 2007/0197917 A1 | 8/2007 | Bagge |
| 2007/0239075 A1 | 10/2007 | Rosenberg et al. |
| 2007/0255355 A1 | 11/2007 | Altshuler et al. |
| 2007/0270745 A1 | 11/2007 | Nezhat et al. |
| 2007/0282318 A1 | 12/2007 | Spooner et al. |
| 2007/0293849 A1 | 12/2007 | Hennings et al. |
| 2008/0014627 A1 | 1/2008 | Merchant et al. |
| 2008/0015435 A1 | 1/2008 | Cribbs et al. |
| 2008/0015624 A1 | 1/2008 | Sonoda et al. |
| 2008/0027328 A1 | 1/2008 | Klopotek et al. |
| 2008/0027384 A1 | 1/2008 | Wang et al. |
| 2008/0058603 A1 | 3/2008 | Edelstein et al. |
| 2008/0058851 A1 | 3/2008 | Edelstein et al. |
| 2008/0091182 A1 | 4/2008 | Mehta |
| 2008/0109023 A1 | 5/2008 | Greer |
| 2008/0147084 A1 | 6/2008 | Bleich et al. |
| 2008/0183164 A1 | 7/2008 | Elkins et al. |
| 2008/0188835 A1 | 8/2008 | Hennings et al. |
| 2008/0195036 A1 | 8/2008 | Merchant et al. |
| 2008/0200845 A1 | 8/2008 | Sokka et al. |
| 2008/0200864 A1 | 8/2008 | Holzbaur et al. |
| 2008/0215039 A1 | 9/2008 | Slatkine et al. |
| 2008/0234609 A1 | 9/2008 | Kreindel et al. |
| 2008/0249526 A1 | 10/2008 | Knowlton |
| 2008/0262527 A1 | 10/2008 | Eder et al. |
| 2008/0269668 A1 | 10/2008 | Keenan et al. |
| 2008/0269687 A1 | 10/2008 | Chong et al. |
| 2008/0306476 A1 | 12/2008 | Hennings et al. |
| 2008/0319356 A1 | 12/2008 | Cain et al. |
| 2008/0319358 A1 | 12/2008 | Lai |
| 2009/0012434 A1 | 1/2009 | Anderson |
| 2009/0018522 A1 | 1/2009 | Weintraub et al. |
| 2009/0024192 A1 | 1/2009 | Mulholland |
| 2009/0048544 A1 | 2/2009 | Rybyanets |
| 2009/0088823 A1 | 4/2009 | Barak et al. |
| 2009/0093864 A1 | 4/2009 | Anderson |
| 2009/0124973 A1 | 5/2009 | D'Agostino et al. |
| 2009/0125013 A1 | 5/2009 | Sypniewski et al. |
| 2009/0156958 A1 | 6/2009 | Mehta |
| 2009/0171255 A1 | 7/2009 | Rybyanets et al. |
| 2009/0192441 A1 | 7/2009 | Gelbart et al. |
| 2009/0198189 A1 | 8/2009 | Simons et al. |
| 2009/0221938 A1 | 9/2009 | Rosenberg et al. |
| 2009/0240188 A1 | 9/2009 | Hyde et al. |
| 2009/0248004 A1 | 10/2009 | Altshuler et al. |
| 2009/0275879 A1 | 11/2009 | Deem et al. |
| 2009/0275899 A1 | 11/2009 | Deem et al. |
| 2009/0275967 A1 | 11/2009 | Stokes et al. |
| 2009/0326439 A1 | 12/2009 | Chomas et al. |
| 2009/0326441 A1 | 12/2009 | Iliescu et al. |
| 2010/0004536 A1 | 1/2010 | Rosenberg |
| 2010/0016761 A1 | 1/2010 | Rosenberg |
| 2010/0017750 A1 | 1/2010 | Rosenberg et al. |
| 2010/0022999 A1 | 1/2010 | Gollnick et al. |
| 2010/0057056 A1 | 3/2010 | Gurtner et al. |

(56) References Cited

U.S. PATENT DOCUMENTS

| | | |
|---|---|---|
| 2010/0137799 A1 | 6/2010 | Imai |
| 2010/0210915 A1 | 8/2010 | Caldwell et al. |
| 2010/0228182 A1 | 9/2010 | Clark, III et al. |
| 2010/0228207 A1 | 9/2010 | Ballakur et al. |
| 2010/0331875 A1 | 12/2010 | Sonoda et al. |
| 2011/0028898 A1* | 2/2011 | Clark, III ........... A61B 18/1477 604/151 |
| 2011/0295230 A1 | 12/2011 | O'Dea |
| 2012/0022504 A1 | 1/2012 | Epshtein et al. |
| 2012/0116375 A1 | 5/2012 | Hennings |
| 2012/0136280 A1 | 5/2012 | Rosenberg et al. |
| 2012/0136282 A1 | 5/2012 | Rosenberg et al. |
| 2012/0165725 A1* | 6/2012 | Chomas ................ A61M 1/008 604/22 |
| 2012/0197242 A1 | 8/2012 | Rosenberg |
| 2012/0277587 A1 | 11/2012 | Adanny et al. |
| 2012/0316547 A1 | 12/2012 | Hennings et al. |
| 2013/0023855 A1 | 1/2013 | Hennings et al. |
| 2013/0096596 A1 | 4/2013 | Schafer |
| 2013/0197315 A1 | 8/2013 | Foley |
| 2013/0197427 A1* | 8/2013 | Merchant et al. ................ 604/24 |
| 2013/0296744 A1 | 11/2013 | Taskinen et al. |
| 2014/0025050 A1 | 1/2014 | Anderson |
| 2014/0031803 A1 | 1/2014 | Epshtein et al. |
| 2014/0107742 A1 | 4/2014 | Mehta |
| 2014/0228834 A1 | 8/2014 | Adanny et al. |
| 2014/0249609 A1 | 9/2014 | Zarsky et al. |
| 2014/0257272 A1 | 9/2014 | Clark, III et al. |
| 2014/0276693 A1 | 9/2014 | Altshuler et al. |
| 2014/0277025 A1 | 9/2014 | Clark, III et al. |
| 2014/0277047 A1 | 9/2014 | Clark, III et al. |
| 2014/0277048 A1 | 9/2014 | Clark, III et al. |
| 2014/0316393 A1 | 10/2014 | Levinson |

FOREIGN PATENT DOCUMENTS

| | | |
|---|---|---|
| CN | 1159908 | 9/1997 |
| CN | 2007/20159899 | 12/2007 |
| CN | 2011/31982 | 10/2008 |
| DE | 3838530 | 5/1990 |
| DE | 4426421 | 2/1996 |
| EP | 148116 | 7/1985 |
| EP | 0224934 | 12/1986 |
| EP | 0278074 | 1/1987 |
| EP | 0327490 | 2/1989 |
| EP | 0384831 | 2/1990 |
| EP | 0953432 | 3/1999 |
| FR | 2643252 | 2/1989 |
| GB | 1216813 | 12/1970 |
| GB | 1577551 | 2/1976 |
| GB | 2327614 | 3/1999 |
| JP | 57-139358 | 8/1982 |
| JP | 2126848 | 5/1990 |
| JP | 2180275 | 7/1990 |
| JP | 5215591 | 8/1993 |
| JP | 2001516625 | 10/2001 |
| JP | 2040283420 | 10/2004 |
| JP | 2005087519 | 4/2005 |
| WO | WO 80/02365 | 11/1980 |
| WO | WO89/05159 | 6/1989 |
| WO | WO89/05160 | 6/1989 |
| WO | WO89/09593 | 10/1989 |
| WO | WO90/01971 | 3/1990 |
| WO | WO92/09238 | 6/1992 |
| WO | WO95/15118 | 6/1995 |
| WO | WO 9729701 | 8/1997 |
| WO | WO9913936 | 3/1999 |
| WO | WO9942138 | 8/1999 |
| WO | WO 00/36982 | 6/2000 |
| WO | WO 03/030984 | 4/2003 |
| WO | WO 03/941597 | 5/2003 |
| WO | WO03/047689 | 6/2003 |
| WO | WO2004/000116 | 12/2003 |
| WO | WO2004/069153 | 8/2004 |
| WO | WO2005/009865 | 2/2005 |
| WO | WO2005/105282 | 11/2005 |
| WO | WO2005/105818 | 11/2005 |
| WO | WO2006/053588 | 5/2006 |
| WO | WO2007102161 | 9/2007 |
| WO | WO2008/139303 | 11/2008 |
| WO | WO2010/020021 | 2/2010 |
| WO | WO2011/017663 | 2/2011 |
| WO | WO2013/059263 | 4/2013 |
| WO | WO 2014/009875 | 1/2014 |
| WO | WO 2014/009826 | 3/2014 |
| WO | WO 2014/060977 | 4/2014 |
| WO | WO 2014/097288 | 6/2014 |
| WO | WO 2014/108888 | 7/2014 |
| WO | WO 2014/141229 | 9/2014 |

OTHER PUBLICATIONS

Bindal, Dr. V. V., et al., Environmental Health Criteria for Ultrasound, International Programme on Chemical Safety, 1982, on. 1-153, World Health Organization.

Brown, Ph.D., S., Director of Plastic Surgery Research, UT Southwestern Medical Center, Dallas, USA, What Happens After Treatment With the UltraShape Device, UltraShape Ltd., Tel Aviv, Israel (2005).

Cartensen, E.L., Allerton Conference for Ultrasonics in Biophysics and Bioengineering: Cavitation, Ultrasound in Med. & Biol., 1987, on. 687-688, vol. 13, Perzamon Journals Ltd.

Chang, Peter P., et al., Thresholds for Inertial Cavitation in Albunex Suspensions Under Pulsed Ultrasound Conditions, IEEE Transactions on Ultrasonics, Ferroelectrics, and Frequency Control, Jan. 2001, pp. 161-170, vol. 48, No. I.

Chen, Wen-Shiang, Ultrasound Contrast Agent Behavior near the Fragmentation Threshold, 2000 IEEE Ultrasonics Symposium, 2000, pp. 1935-1938.

Dijkmans, P.A., et al., Microbubbles and Ultrasound: From Diagnosis to Therapy, Eur J Echocardiography, 2004, pp. 245-256, vol. 5, Elsevier Ltd., The Netherlands.

Feril, L.B., et al., Enhanced Ultrasound-Induced Apoptosis and Cell Lysis by a Hypnotic Medium, International Journal of Radiation Biology, Feb. 2004, PO. 165-175, vol. 2, Taylor & Francis Ltd., United Kingdom.

Feril, Jr., Loreto B., et al., Biological Effects of Low Intensity Ultrasound: The Mechanism Involved, and its Implications on Therapy and on Biosafety of Ultrasound, J. Radial. Res., 2004, nn. 479-489, vol. 45.

Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.

Hanscom, D.R., Infringement Search Report prepared for K. Angela Macfarlane, Esq., Chief Technology Counsel, The Foundry, Nov. 15, 2005.

Hexsel, D. et al, Side-By-Side Comparison of Areas with and without Cellulite Depressions Using Magnetic Resonance Imaging, American Society for Dermatologic Surgery, Inc., 2009, pp. 1-7, Wiley Periodicals, Inc.

Hexsel, M.D., Doris Maria, et al., Subcision: a Treatment for Cellulite, International journal of Dermatology 2000, on. 539-544, vol. 39.

Holland, Christy K., et al., In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. I.

http://www.thefreedictionary.com/chamber, definition of the term "chamber" retrieved Jun. 16, 2013.

International Search Report dated Apr. 9, 2012 from corresponding International Patent Application No. PCT/US11/62449.

Internet Web Site—www.icin.nllread/project 21, The Interuniversity Cardiology Institute of the Netherlands, 3 pgs., visited Dec. 22, 2005.

Internet Web Site—www.turnwoodinternational.comiCellulite.htm, Acthyderm Treating Cellulite, Aug. 5, 2005, 4pgs., visited Jan. 12, 2006.

(56) References Cited

OTHER PUBLICATIONS

Japan Office Action—Application No. JP2000-190976 dated Jul. 11, 2000.
Khan, M. et al., Treatment of cellulite—Part I. Pathophysiology, J Am Acad Dermatol, 2009, vol. 62, No. 3, pp. 361-370.
Khan, M. et al., Treatment of cellulite—Part II. Advances and controversies, J Am Acad Dermatol, 2009, vol. 62, No. 3, pp. 373-384.
Lawrence, M.D., N., et al., The Efficacy of External Ultrasound-Assisted Liposuction: A Randomized Controlled Trial, Dermatol SUll!, Apr. 2000, nn. 329-332, vol. 26, Blackwell Science, Inc.
Michaelson, Solomon M., et al., Fundamental and Applied Aspects of Nonionizing Radiation, Rochester International Conference on Environmental Toxicity, 75h, 1974, pp. 275-299, Plenum Press, New York and London.
Miller, Douglas 1., A Review of the Ultrasonic Bioeffects of Microsonation, Gas-Body Activiation, and Related Cavitation-Like Phenomena, Ultrasound in Med. & Biol., 1987, pp. 443-470, vol. 13, Pergamon Journals Ltd.
Miller, Douglas 1., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.
Miller, Douglas L., et al., On the Oscillation Mode of Gas-filled Micropores, 1. Acoust. Soc. Am., 1985, pp. 946-953, vol. 77 (3).
Miller, Douglas L., Gas Body Activation, Ultrasonics, Nov. 1984, pp. 261-269, vol. 22, No. 6, Butterworth & Co. Ltd.
Miller, Douglas L., Microstreaming Shear As a Mechanism of Cell Death in Elodea Leaves Exposed to Ultrasound, Ultrasound in Med. & Biol., 1985, op. 285-292, vol. II, No. 2, Pergamon Press, U.S.A.

Miller, Morton W., et al., A Review of In Vitro Bioeffects of Inertial Ultrasonic Cavitation From a Mechanistic Perspective, Ultrasound in Med. & Biol., 1996, nn. 1131-1154, vol. 22, No. 9.
Nyborg, Dr. Wesley L., Physical Mechanisms for Biological Effects of Ultrasound, HEW Publicaton (FDA) 78-8062, Sep. 1977, pp. 1-59, U.S. Department of Health, Education, and Welfare, Rockville, Maryland.
Orentreich, D. et al., Subcutaneous Incisionless (Subcision) Surgery for the Correction of Depressed Scars and Wrinkles, Dermatol Surg, 1995:21,1995, pp. 543-549, Esevier Science Inc.
Carstensen, E.L. et al, Biological Effects of Acoustic Cavitation, University of Rochester, Rochester, New York, May 13-16, 1985.
Rohrich, M.D., R.I., et al., Comparative Lipoplasty Analysis of in Vivo-Treated Adipose Tissue, Plastic and Reconstructive SUfl'erv, May 2000, pn, 2152-2158, vol. 105, No. 6.
Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.
Scheinfeld, M.D., J.D. Faad, N.S., Liposuction Techniques: External Ultrasound-Assisted, eMedicine.com, Inc., 2005.
Villarraga, M.D., H.R., et al., Destruction of Contrast Microbubbles During Ultrasound Imaging at Conventional Power Output, Journal of the American Society of Echocardiography, Oct. 1997, pp. 783-791.
Vivino, Alfred A., et al., Stable Cavitation at low Ultrasonic Intensities Induces Cell Death and Inhibits H-TdR Incorporation by Con-A-Stimulated Murine Lymphocytes in Vitro, Ultrasound in Med. & Biol., 1985, pp. 751-759, vol. II, No. 5, Pergamon Press Ltd.
Weaver, James C. Electroporation; a general phenomenon for manipulating cells and tissues. J Cell Biochem. Apr. 1993; 51(4):426-35.

* cited by examiner

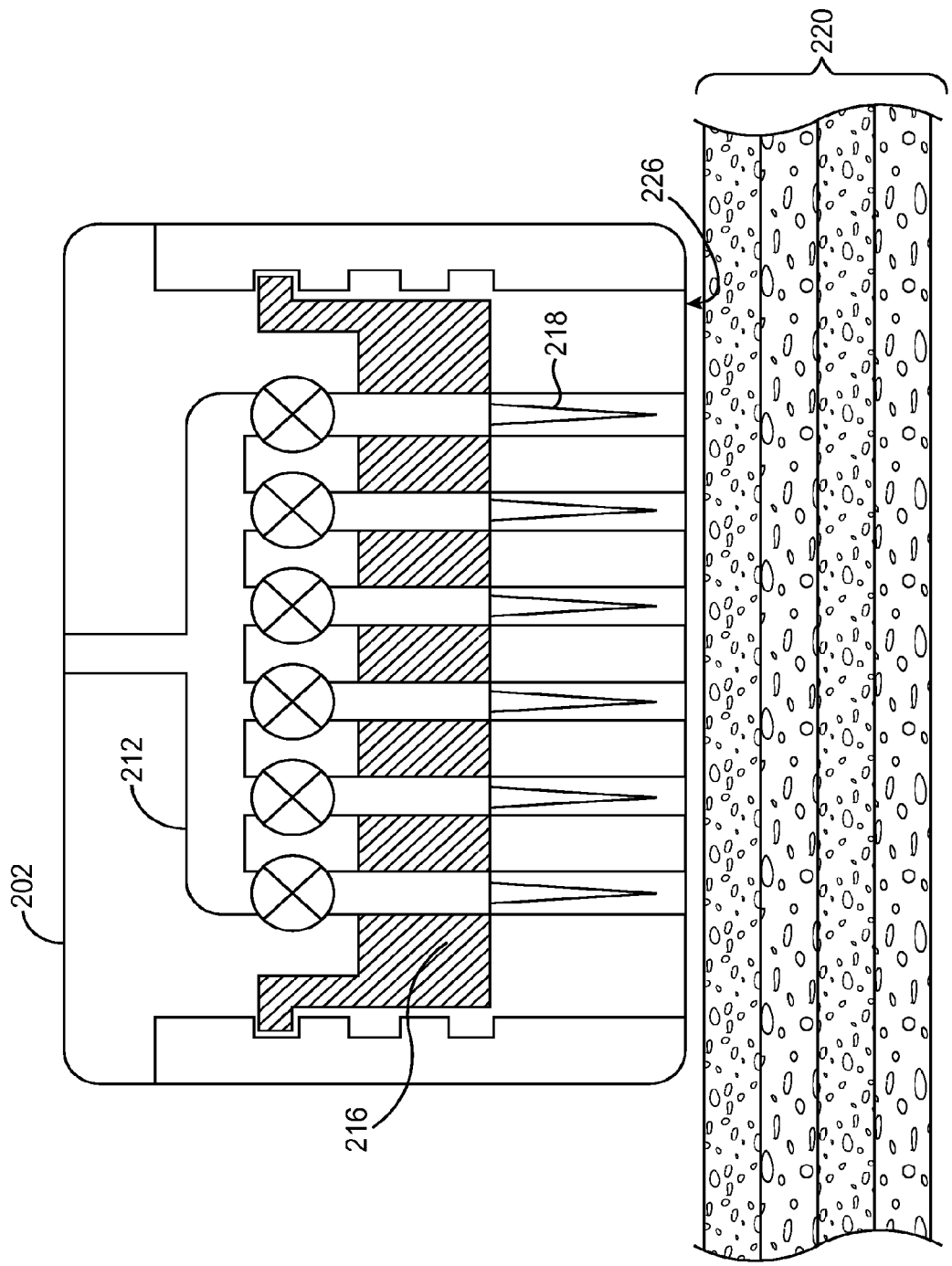

SYSTEMS AND DEVICES FOR SELECTIVE CELL LYSIS AND METHODS OF USING SAME

CLAIM FOR PRIORITY/REFERENCE TO CO PENDING APPLICATIONS

This application is a continuation of U.S. patent application Ser. No. 13/799,377, filed on Mar. 13, 2013, now U.S. Pat. No. 9,079,001, which is a continuation of U.S. patent application Ser. No. 11/771,951, filed Jun. 29, 2007, now abandoned, wherein Ser. No. 11/771,951 is a continuation-in-part of U.S. patent application Ser. No. 11/515,634, filed Sep. 5, 2006, now abandoned, wherein Ser. No. 11/771,951 is a continuation-in-part of U.S. patent application Ser. No. 11/334,805, filed Jan. 17, 2006, now U.S. Pat. No. 7,601,128, wherein Ser. No. 11/771,951 is a continuation-in-part of U.S. patent application Ser. No. 11/334,794, filed Jan. 17, 2006, now U.S. Pat. No. 7,588,547, and wherein Ser. No. 11/771,951 is a continuation-in-part of U.S. patent application Ser. No. 11/292,950, filed Dec. 2, 2005, now U.S. Pat. No. 7,967,763, the entirety of each of which are incorporated herein by reference.

FIELD OF THE INVENTION

The present invention relates to a microbubble generation device and a system for selectively lysing cells by cavitating microbubbles.

BACKGROUND OF THE INVENTION

Gynoid lipodystrophy is a localized metabolic disorder of the subcutaneous tissue which leads to an alteration in the topography of the cutaneous surface (skin), or a dimpling effect caused by increased fluid retention and/or proliferation of adipose tissue in certain subdermal regions. This condition, commonly known as cellulite, affects over 90% of post-pubescent women, and some men. Cellulite commonly appears on the hips, buttocks and legs, but is not necessarily caused by being overweight, as is a common perception. Cellulite is formed in the subcutaneous level of tissue below the epidermis and dermis layers. In this region, fat cells are arranged in chambers surrounded by bands of connective tissue called septae. As water is retained, fat cells held within the perimeters defined by these fibrous septae expand and stretch the septae and surrounding connective tissue. Furthermore, adipocyte expansion from weight gain may also stretch the septae. Eventually this connective tissue contracts and hardens (scleroses) holding the skin at a non-flexible length, while the chambers between the septae continue to expand with weight gain, or water gain. This results in areas of the skin being held down while other sections bulge outward, resulting in the lumpy, "orange peel" or "cottage cheese" appearance on the skin surface.

Even though obesity is not considered to be a root cause of cellulite, it can certainly worsen the dimpled appearance of a cellulitic region due to the increased number of fat cells in the region. Traditional fat extraction techniques such as liposuction that target deep fat and larger regions of the anatomy, can sometimes worsen the appearance of cellulite since the subdermal fat pockets remain and are accentuated by the loss of underlying bulk (deep fat) in the region. Many times liposuction is performed and patients still seek therapy for remaining skin irregularities, such as cellulite.

A variety of approaches for treatment of skin irregularities such as cellulite and removal of unwanted adipose tissue have been proposed. For example, methods and devices that provide mechanical massage to the affected area, through either a combination of suction and massage or suction, massage and application of energy, in addition to application of various topical agents are currently available. Developed in the 1950's, mesotherapy is the injection of various treatment solutions through the skin that has been widely used in Europe for conditions ranging from sports injuries to chronic pain, to cosmetic procedures to treat wrinkles and cellulite. The treatment consists of the injection or transfer of various agents through the skin to provide increased circulation and the potential for fat oxidation, such as aminophylline, hyaluronic acid, novocaine, plant extracts and other vitamins. The treatment entitled Acthyderm (Tumwood International, Ontario, Canada) employs a roller system that electroporates the stratum corneum to open small channels in the dermis, followed by the application of various mesotherapy agents, such as vitamins, antifibrotics, lypolitics, anti-inflammatories and the like.

Massage techniques that improve lymphatic drainage were tried as early as the 1930's. Mechanical massage devices, or Pressotherapy, have also been developed such as the "Endermologie" device (LPG Systems, France), the "Synergie" device (Dynatronics, Salt Lake City, Utah) and the "Silklight" device (Lumenis, Tel Aviv, Israel), all utilizing subdermal massage via vacuum and mechanical rollers. Other approaches have included a variety of energy sources, such as Cynosure's "TriActive" device (Cynosure, Westford, Mass.) utilizing a pulsed semiconductor laser in addition to mechanical massage, and the "Cellulux" device (Palomar Medical, Burlington, Mass.) which emits infrared light through a cooled chiller to target subcutaneous adipose tissue. The "VelaSmooth" system (Syneron, Inc., Yokneam Illit, Israel) employs bipolar radiofrequency energy in conjunction with suction to increase metabolism in adipose tissue, and the "Thermacool" device (Thermage, Inc., Hayward, Calif.) utilizes radiofrequency energy to shrink the subdermal fibrous septae to treat wrinkles and other skin defects. Other energy based therapies such as electrolipophoresis, using several pairs of needles to apply a low frequency interstitial electromagnetic field to aid circulatory drainage have also been developed. Similarly, non-invasive ultrasound is used in the "Dermosonic" device (Symedex Medical, Minneapolis, Minn.) to promote reabsorption and drainage of retained fluids and toxins.

Another approach to the treatment of skin irregularities such as scarring and dimpling is a technique called subcision. This technique involves the insertion of a relatively large gauge needle subdermally in the region of dimpling or scarring, and then mechanically manipulating the needle below the skin to break up the fibrous septae in the subdermal region. In at least one known method of subcision, a local anesthetic is injected into the targeted region, and an 18 gauge needle is inserted 10-20 mm below the cutaneous surface. The needle is then directed parallel to the epidermis to create a dissection plane beneath the skin to essentially tear through, or "free up" the tightened septae causing the dimpling or scarring. Pressure is then applied to control bleeding acutely, and then by the use of compressive clothing following the procedure. While clinically effective in some patients, pain, bruising, bleeding and scarring can result. The known art also describes a laterally deployed cutting mechanism for subcision, and a technique employing an ultrasonically assisted subcision technique.

Certain other techniques known as liposuction, tumescent liposuction, lypolosis and the like, target adipose tissue in the subdermal and deep fat regions of the body. These techniques may include also removing the fat cells once they are disrupted, or leaving them to be resorbed by the body's immune/lymphatic system. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient.

The "Lysonix" system (Mentor Corporation, Santa Barbara, Calif.) utilizes an ultrasonic transducer on the handpiece of the suction cannula to assist in tissue disruption (by cavitation of the tissue at the targeted site). Liposonix (Bothell, Wash.) and Ultrashape (TelAviv, Israel) employ the use of focused ultrasound to destroy adipose tissue noninvasively. In addition, cryogenic cooling has been proposed for destroying adipose tissue. A variation on the traditional liposuction technique known as tumescent liposuction was introduced in 1985 and is currently considered by some to be the standard of care in the United States. It involves the infusion of tumescent fluids to the targeted region prior to mechanical disruption and removal by the suction cannula. The fluids may help to ease the pain of the mechanical disruption, while also swelling the tissues making them more susceptible to mechanical removal. Various combinations of fluids may be employed in the tumescent solution including a local anesthetic such as lidocaine, a vasoconstrictive agent such as epinephrine, saline, potassium and the like. The benefits of such an approach are detailed in the articles, "Laboratory and Histopathologic Comparative Study of Internal Ultrasound-Assisted Lipoplasty and Tumescent Lipoplasty" Plastic and Reconstructive Surgery, Sep. 15, (2002) 110:4, 1158-1164, and "When One Liter Does Not Equal 1000 Milliliters: Implications for the Tumescent Technique" Dermatol. Surg. (2000) 26: 1024-1028, the contents of which are expressly incorporated herein by reference in their entirety.

Various other approaches employing dermatologic creams, lotions, vitamins and herbal supplements have also been proposed to treat cellulite. Private spas and salons offer cellulite massage treatments that include body scrubs, pressure point massage, essential oils, and herbal products using extracts from plant species such as seaweed, horsetail and *clematis* and ivy have also been proposed. Although a multitude of therapies exist, most of them do not provide a lasting effect on the skin irregularity, and for some, one therapy may cause the worsening of another (as in the case of liposuction causing scarring or a more pronounced appearance of cellulite). Yet other treatments for cellulite have negative side effects that limit their adoption. Most therapies require multiple treatments on an ongoing basis to maintain their effect at significant expense and with mixed results.

Medical ultrasound apparatus and methods are generally of two different types. One type of medical ultrasound wave generating device known in the art is that which provides high intensity focused ultrasound or high acoustic pressure ultrasound for tissue treatment, for example for tumor destruction. High intensity or high acoustic pressure ultrasound is capable of providing direct tissue destruction. High intensity or high acoustic pressure ultrasound is most commonly focused at a point in order to concentrate the energy from the generated acoustic waves in a relatively small focus of tissue. However, another type of medical ultrasound is a lower intensity and less focused type of ultrasound that is used for diagnostic imaging and physical therapy applications. Low acoustic pressure ultrasound is commonly used, for example, for cardiac imaging and fetal imaging. Low acoustic pressure ultrasound may be used for tissue warning, without tissue disruption, in physical therapy applications. Low acoustic pressure ultrasound, using power ranges for diagnostic imaging, generally will not cause any significant tissue disruption when used for limited periods of time in the absence of certain enhancing agents.

Methods and apparatus of using high intensity focused ultrasound to disrupt subcutaneous tissues directly has been described in the known art. Such techniques may utilize a high intensity ultrasound wave that is focused on a tissue within the body, thereby causing a localized destruction or injury to cells. The focusing of the high intensity ultrasound may be achieved utilizing, for example, a concave transducer or an acoustic lens. Use of high intensity focused ultrasound to disrupt fat, sometimes in combination with removal of the fat by liposuction, has been described in the known prior art. Such use of high intensity focused ultrasound should be distinguished from the low acoustic pressure ultrasound.

In light of the foregoing, it would be desirable to provide methods and apparatus for treating skin irregularities such as cellulite and to provide a sustained aesthetic result to a body region, such as the face, neck, arms, legs, thighs, buttocks, breasts, stomach and other targeted regions which are minimally or non-invasive. It would also be desirable to provide methods and apparatus for treating skin irregularities that enhance prior techniques and make them less invasive and subject to fewer side effects.

Therefore, there has been recognized by those skilled in the art a need for an apparatus and method for the use of low intensity ultrasound to treat subcutaneous tissues. Use of low intensity ultrasound, in the power ranges of diagnostic ultrasound, would be safer to use, have fewer side effects, and could be used with less training. The present invention fulfills these needs and others.

SUMMARY OF THE INVENTION

Disclosed is a device for generating microbubbles in a gas and liquid mixture and injection device, which includes a housing defining a mixing chamber; means for mixing solution contained in the mixing chamber to generate microbubbles in the solution; and a needle array removably attached to the housing and in fluid connection with the mixing chamber, the needle array including at least one needle.

The mixing chamber may include a first mixing chamber m fluid communication with a second mixing chamber. Moreover, the mixing means may include means for expressing a solution of fluid and gas between the first and second mixing chambers to generate microbubbles in the solution.

The device may further include a fluid reservoir in fluid connection with at least one of the first and second mixing chambers; and a source of gas in fluid connection with at least one of the first and second mixing chambers. Optionally, the fluid reservoir and/or the mixing chamber(s) may be thermally insulated and/or include means for maintaining the fluid at a predetermined temperature. Still further, the source of gas may be room air, or may include air, oxygen, carbon dioxide, perfluoropropane or the like which may be maintained at greater than atmospheric pressure.

The solution expressing means may include first and second pistons mounted for reciprocation within the first and second mixing chambers.

Still further, the device may include means for reciprocating the first and second pistons to express fluid and gas between the first and second cylinders to create a microbubble solution. The reciprocating means may be a source of compressed air; and the first and second cylinders may be pneumatic cylinders.

The device may include a needle deployment mechanism operably connected to the needle array for deploying the at least one needle(s) between a retracted and an extended position. The needle array may include at least two needles and the needle deployment mechanism selectively deploys one or more of the at least two needles between the retracted and the extended position. Still further, the needle deployment mechanism may include at least one of a pneumatic piston, an electric motor, and a spring.

The device may include at least one pressure sensor for measuring tissue apposition pressure. The sensor may be provided on either or both of the housing and the needle array. Deployment of the at least one needle may be inhibited if a measured apposition pressure values falls beneath an initial threshold value or exceeds a secondary threshold value. The device may include two or more sensors wherein deployment of the at least one needle is inhibited if a difference in measured apposition pressure values between any two sensors exceeds a threshold value.

The aforementioned mixing means may include at least one of a blade, paddle, whisk, and semi-permeable membrane positioned within the mixing chamber. The mixing means may further include one of a motor and a pneumatic source operably coupled to the at least one of a blade, paddle, whisk, and semi-permeable membrane.

The device of the present invention may include tissue apposition means for pulling the needle array into apposition with tissue. The tissue apposition means may include at least one vacuum orifice defined in at least one of the housing and the needle array, whereby the vacuum orifice transmits suction from a source of partial vacuum to tissue bringing the needle array into apposition with the tissue. The vacuum orifice may be formed in the needle array, and the at least one needle may be positioned within the vacuum orifice. Still further, the vacuum orifice may define a receptacle, whereby tissue is pulled at least partially into the receptacle when the vacuum orifice transmits suction from the source of partial vacuum.

In some embodiments, the needle array includes a tissue apposition surface; and the tissue apposition means further includes at least one flange mounted on the tissue apposition surface and surrounding the vacuum orifice.

The device of the present invention may include means for adjusting a needle insertion depth of the at least one needle. The needle array may include at least two needles and the insertion depth adjustment means may individually adjust the insertion depth of each needle. In one embodiment, the needle insertion depth adjustment means may include a plurality of discrete needle adjustment depths. Alternatively, the needle insertion depth adjustment means provides continuous adjustment of the needle adjustment depth. Still further, the needle insertion depth adjustment means may include a readout and/or a display indicative of the needle adjustment depth.

According to one embodiment, the needle array includes a tissue apposition surface; and the at least one needle includes a distal end, the at least one needle being moveable between a retracted position in which the distal end of the needle is maintained beneath the tissue apposition surface and an extended position in which the distal end of the needle extends beyond the tissue apposition surface.

According to one embodiment an ultrasound transducer is operably connected to one of the needle array, the housing and the at least one needle.

According to one aspect, the needle array may generally surround the ultrasound transducer. Alternatively, the ultrasound transducer may generally surround the needle array. Moreover, the ultrasound transducer may be integrally formed with the needle array.

The device may further include a fluid pressurization mechanism m fluid communication with the at least one needle.

Still further, the device may include means for controlling a volume and pressure of fluid dispensed from the fluid reservoir into the mixing chamber. Moreover the device may include means for controlling the volume, pressure, and rate at which fluid or solution is injected into the tissue.

A machine readable identifier may be provided on the needle array. The identifier may be used to uniquely identify the ultrasound transducer, needle array and/or characteristics of the needle array.

According to one embodiment, the device includes a machine readable identifier on the needle array and means for reading the identifier operably connected to the needle deployment mechanism. Optionally, the needle deployment mechanism inhibits deployment of the at least one needle unless the identifier reading means authenticates the identifier. Moreover, the needle deployment mechanism may optionally accumulate the number of times the needle array associated with a given identifier is deployed and inhibit deployment of the at least one needle if the accumulated number needle deployments associated with the identifier exceeds a predetermined value.

According to one embodiment, the device includes a machine readable identifier on the needle array and means for reading the identifier operably connected to the fluid pressurization mechanism, wherein the fluid pressurization mechanism adjusts the fluid injection pressure in response to information read from the identifier.

Also disclosed is a system comprising, a container containing a measured amount of a solution including at least one of a vasoconstrictor, a surfactant, and an anesthetic, the solution comprising a liquid and at least one of a gas and a fluid; a needle array in fluid connection with the container, the needle array including at least one needle. The gas is at least partially dissolved and may be fully dissolved in the fluid. Optionally, the solution container is enclosed, and the solution is maintained at greater than atmospheric pressure.

The aforementioned system may include an ultrasound transducer apparatus capable of operating in at least one of first, second, third, and fourth energy settings, wherein the first energy setting is selected to facilitate the absorption of solution by the tissue, the second energy setting is selected to facilitate stable cavitation, the third energy setting is selected to facilitate transient cavitation, and the fourth energy setting is selected to facilitate pushing bubbles within tissue. The transducer apparatus may include first and second transducers, wherein the first transducer facilitates popping of bubbles and the second transducer facilitates bringing dissolved gas out of solution. According to one embodiment, the transducer apparatus produces at least one of unfocussed and defocused ultrasound waves.

Also disclosed is a method for selectively lysing cells, comprising: percutaneously injecting a solution including at least one of a vasoconstrictor, a surfactant, and an anesthetic into subcutaneous tissue, insonating the tissue with ultrasound setting to distribute the solution by acoustic radiation force; and insonating the tissue at a second ultrasound setting to induce cell uptake of the solution and thereby lyse the cells.

Also disclosed is a method for selectively lysing cells, comprising: percutaneously injecting a microbubble solution into subcutaneous tissue; insonating the tissue at a first ultrasound setting to distribute the solution and push the microbubble against walls of the cells by acoustic radiation force; and insonating the tissue at a second ultrasound setting to induce transient cavitation. The solution may include at least one of a vasoconstrictor, a surfactant, and an anesthetic.

Also disclosed is a method for selectively lysing cells, comprising: percutaneously injecting a solution into subcutaneous tissue, the solution containing at least one of a dissolved gas and a partially dissolved gas; insonating the tissue to induce stable cavitation and generate microbubbles; insonating the tissue with ultrasound to distribute the solution and push the microbubble against walls of the cells by acoustic radiation force; insonating the tissue with ultrasound to induce transient cavitation. The solution may include at least one of a vasoconstrictor, a surfactant, and an anesthetic.

Each of the aforementioned embodiments may include a needle or needles having a texture encouraging the creation of micro bubbles.

BRIEF DESCRIPTION OF THE DRAWINGS

Further features of the invention, its nature and various advantages will be more apparent from the accompanying drawings and the following detailed description, in which:

FIGS. 8A and 8B show the fluid injection device in a retracted and fully extended position;

DETAILED DESCRIPTION OF THE PREFERRED EMBODIMENTS

Figure 1A:
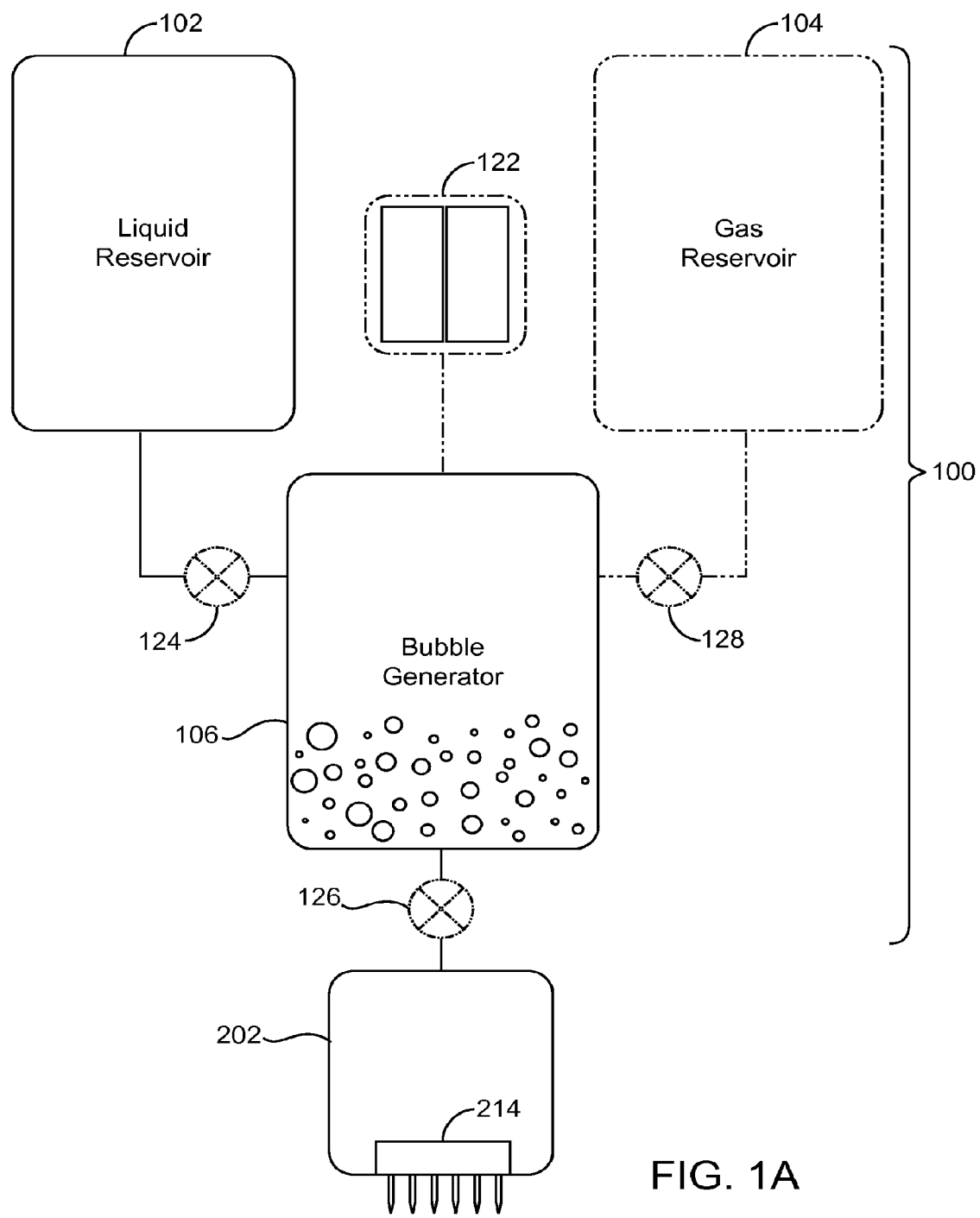
FIGS. 1A and 1B are block diagrams of a bubble generator according to the present invention.

One aspect of the present invention relates to a device for generating a microbubble solution and for a system using the device to selectively lyse tissue.

According to a first embodiment of the invention the microbubble solution includes a fluid or mixture containing one or more of the following: active bubbles, partially dissolved bubbles, a saturated or supersaturated liquid containing fully dissolved bubbles or a material/chemical which generates bubbles in situ. The bubbles may be encapsulated within a lipid or the like, or may be unencapsulated (free) bubbles.

Active bubbles refer to gaseous or vapor bubbles which may include encapsulated gas or unencapsulated gas. These active bubbles may or may not be visible to the naked eye. Dissolved bubbles refer to gas which has dissolved into the liquid at a given pressure and temperature but which will come out of solution when the temperature and/or pressure of the solution changes or in response to ultrasound insonation. The microbubbles may come out of solution in situ, i.e., after the solution is injected into the tissue. This may, for example, occur when the solution reaches the temperature of the tissue or when the tissue is subjected to ultrasound insonation. Alternatively, the microbubble may come out of solution before the solution is injected into the tissue when reaching atmospheric pressure. Thus, the bubbles may come out of solution before or after the solution is injected into the tissue.

As noted, the solution includes a liquid (fluid) and a gas which may or may not be dissolved in the liquid. By manner of illustration, the liquid portion of enhancing agent may include an aqueous solution, isotonic saline, normal saline, hypotonic saline, hypotonic solution, or a hypertonic solution. The solution may optionally include one or more additives/agents to raise the pH (e.g., sodium bicarbonate) or a buffering agent such as known in the art. By manner of illustration the gaseous portion of the solution may include air drawn from the room ("room air" or "ambient air"), oxygen, carbon dioxide, perfluoropropane, argon, hydrogen, or a mixture of one or more of these gases. However, the invention is not limited to any particular gas. There are a number of candidate gas and liquid combinations, the primary limitation being that both the gas and the liquid must be biocompatible, and the gas must be compatible with the liquid.

According to a presently preferred embodiment the liquid portion of the microbubble solution includes hypotonic buffered saline and the gaseous portion includes air.

It should be noted that the biocompatibility of overall solution depends on a variety of factors including the biocompatibility of the liquid and gas, the ratio of gas to liquid, and the size of the micro bubbles. If the micro bubbles are too large they may not reach the target tissue. Moreover, if the bubbles are too small they may go into solution before they can be used therapeutically. As will be explained in further detail below, the microbubble solution of the present invention may include a distribution of different sized microbubbles. Thus it is anticipated that the solution may contain at least some microbubbles which are too small to be therapeutically useful as well as some which are larger than the ideal size. It is anticipated that a filter, filtering mechanism or the like may be provided to ensure that bubbles larger than a threshold size are not injected into the tissue.

It should further be appreciated that "biocompatible" is a relative term in that living tissue may tolerate a small amount of a substance whereas a large amount of the same substance may be toxic with both dose and dosage as considerations. Thus, the biocompatibility of the microbubble solution of the present invention should be interpreted in relation to the amount of solution being infused, the size of the microbubbles, and the ratio of gas to liquid. Moreover, since selective cell lysis is one of the objects of the present invention, the term biocompatible should be understood to include a mixture or solution which may result in localized cell lysis alone or in conjunction with ultrasound insonation.

The microbubble solution according to the present invention may include one or more additives such as a surfactant to stabilize the microbubbles, a local anesthetic, a vasodilator, and a vasoconstrictor. By manner of illustration the local anesthetic may be lidocaine and the vasoconstrictor may be epinephrine. Table 1 is a non-exclusive list of other vasoconstrictors which may be included in the micro bubble solution of the present invention. Table 2 is a non-exclusive list of other local anesthetics which may be included in the micro bubble solution of the present invention. Table 3 is a non-exclusive list of gaseous anesthetics which may be included in the gaseous portion of the solution of the present invention. Table 4 is a non-exclusive list of surfactants which may be included in the solution of the present invention.

TABLE 1

Vasoconstrictors

Norepinephrine
Epinephrine
Angiotensin II
Vasopressin
Endothelin

TABLE 2

Anesthetics (Local)

Amino esters
Benzocaine
Chloroprocaine
Cocaine
Procaine
Tetracaine
Amino amides
Bupivacaine
Levobupivacaine
Lidocaine
Mepivacaine
Prilocaine
Ropivacaine
Articaine
Trimecaine

TABLE 3

Anesthetics (gaseous)

Halo thane
Desflurane
Sevoflurane
Isoflurane
Enflurane

TABLE 4

Surfactants

Anionic (based on sulfate, sulfonate or carboxylate anions)
    Sodium dodecyl sulfate (SDS), ammonium lauryl sulfate, and other alkyl
    sulfate salts
    Sodium laureth sulfate, also known as sodium lauryl ether sulfate (SLES)
    Alkyl benzene sulfonate
    Soaps, or fatty acid salts
Cationic (based on quaternary ammonium cations)
    Cetyl trimethylammonium bromide (CTAB) a.k.a. hexadecyl trimethyl
    ammonium bromide, and other alkyltrimethylammonium salts
    Cetylpyridinium chloride (CPC)
    Polyethoxylated tallow amine (POEA)
    Benzalkonium chloride (BAC)
    Benzethonium chloride (BZT)
Zwitterionic (amphoteric)
    Dodecyl betaine
    Dodecyl dimethylamine oxide
    Cocamidopropyl betaine
    Coco ampho glycinate
Nonionic
    Alkyl poly(ethylene oxide) called Poloxamers or Poloxamines)
    Alkyl polyglucosides, including:
        Octyl glucoside
        Decyl maltoside
Fatty alcohols
    Cetyl alcohol
    Oleyl alcohol
Cocamide MEA, cocamide DEA, cocamide TEA The enhancing solution may further include a buffering agent such as sodium bicarbonate. Table 5 is a non-exclusive list of buffers which may be included in the solution of the present invention.

TABLE 5

| Buffer | |
|---|---|
| $H_3PO_4/NaH_2PO_4$ ($pK_{a1}$) | $NaH_2PO_4/Na_2HPO_4$ ($pK_{a2}$) |
| 1,3-Diaza-2,4-cyclopentadiene and Glyoxaline (Imidazole) | N-Tris(hydroxymethyl)methyl-2-aminoethanesulfonic acid (TES) |
| ampholyte N-(2-hydroxyethyl) piperazine-N'-2-hydroxypropanesulfonic acid (HEPPSO) | N-2-Hydroxyethylpiperazine-N'-2-ethanesulfonic acid (HEPES) |
| Acetic acid | Citric acid ($pK_{a1}$) |
| N-Tris(hydroxymethyl)methyl-3-aminopropanesulfonic acid (TAPS) | Triethanolamine (2,2',2''-Nitrilotriethanol Tris(2-hydroxyethyl)amine) |
| Bis(2-hydroxyethyl)iminotris(hydroxymethyl)methane (Bis-Tris) | N-[Tris(hydroxymethyl)methyl]glycine, 3-[(3-Cholamidopropyl)dimethylammonio]propanesulfonic acid (Tricine) |
| Cacodylic acid | 2-Amino-2-(hydroxymethyl)-1,3-propanediol (Tris) |
| $H_2CO_3/NaHCO_3$ ($pK_{a1}$) | Glycine amide |
| Citric acid ($pK_{a3}$) | N,N-Bis(2-hydroxyethyl)glycine (Bicine) |
| 2-(N-Morpholino)ethanesulfonic Acid (MES) | Glycylglycine ($pK_{a2}$) |
| N-(2-Acetamido)iminodiacetic Acid (ADA) | Citric acid ($pK_{a2}$) |
| Bis-Tris Propane ($pK_{a1}$) | Bis-Tris Propane ($pK_{a2}$) |

TABLE 5-continued

| Buffer | |
|---|---|
| Piperazine-1,4-bis(2-ethanesulfonic acid) (PIPES) | N-(2-Acetamido)-2-aminoethanesulfonic acid (ACES) |
| Boric acid ($H_3BO_3/Na_2B_4O_7$) | N-Cyclohexyl-2-aminoethanesulfonic acid (CHES) |
| Glycine ($pK_{a1}$) | Glycine ($pK_{a2}$) |
| N,N-Bis(2-hydroxyethyl)-2-aminoethanesulfonic acid (BES) | $NaHCO_3/Na_2CO_3$ ($pK_{a2}$) |
| 3-Morpholinopropanesulfonic acid (MOPS) | N-Cyclohexyl-3-aminopropanesulfonic acid (CAPS) |
| $Na_2HPO_4/Na_3PO_4$ ($pK_{a3}$) | Hexahydropyridine (Piperidine) |

*The anhydrous molecular weight is reported in the table. Actual molecular weight will depend on the degree of hydration.

It should be noted that like reference numerals are intended to identify like parts of the invention, and that dashed lines are intended to represent optional components.

FIG. 1A depicts a first embodiment of a device 100 for generating micro bubbles in the enhancing solution. The device 100 consists of a liquid reservoir 102, a gas vapor reservoir 104 (shown in dashed lines) and a bubble generator 106. The bubble generator 106 is a vessel or vessels in which the fluid and gas are mixed. Fluid from the liquid reservoir 102 and gas/vapor from the gas reservoir 104 flow into the bubble generator 106 and are mixed to create micro bubbles and/or supersaturate the fluid.

The device 100 may include a fluid metering device 124 (shown in dashed lines) controlling the amount of fluid dispensed into the bubble generator 106 and/or a fluid metering device 126 (shown in dashed lines) controlling the amount of micro bubble solution to be injected into the tissue. The device 100 may further include a gas metering device 128 (shown in dashed lines) used to control the amount of gas dispensed into the bubble generator 106. The device 100 depicted in FIG. 1A includes both of the fluid metering devices 124 and 126 and the gas metering device 128; however, in practice one or more of these devices may be eliminated. As noted previously, two or more components may be integrated together. For example, the fluid metering device 124 may be integrated into the fluid injection device 202.

Figure 1B:
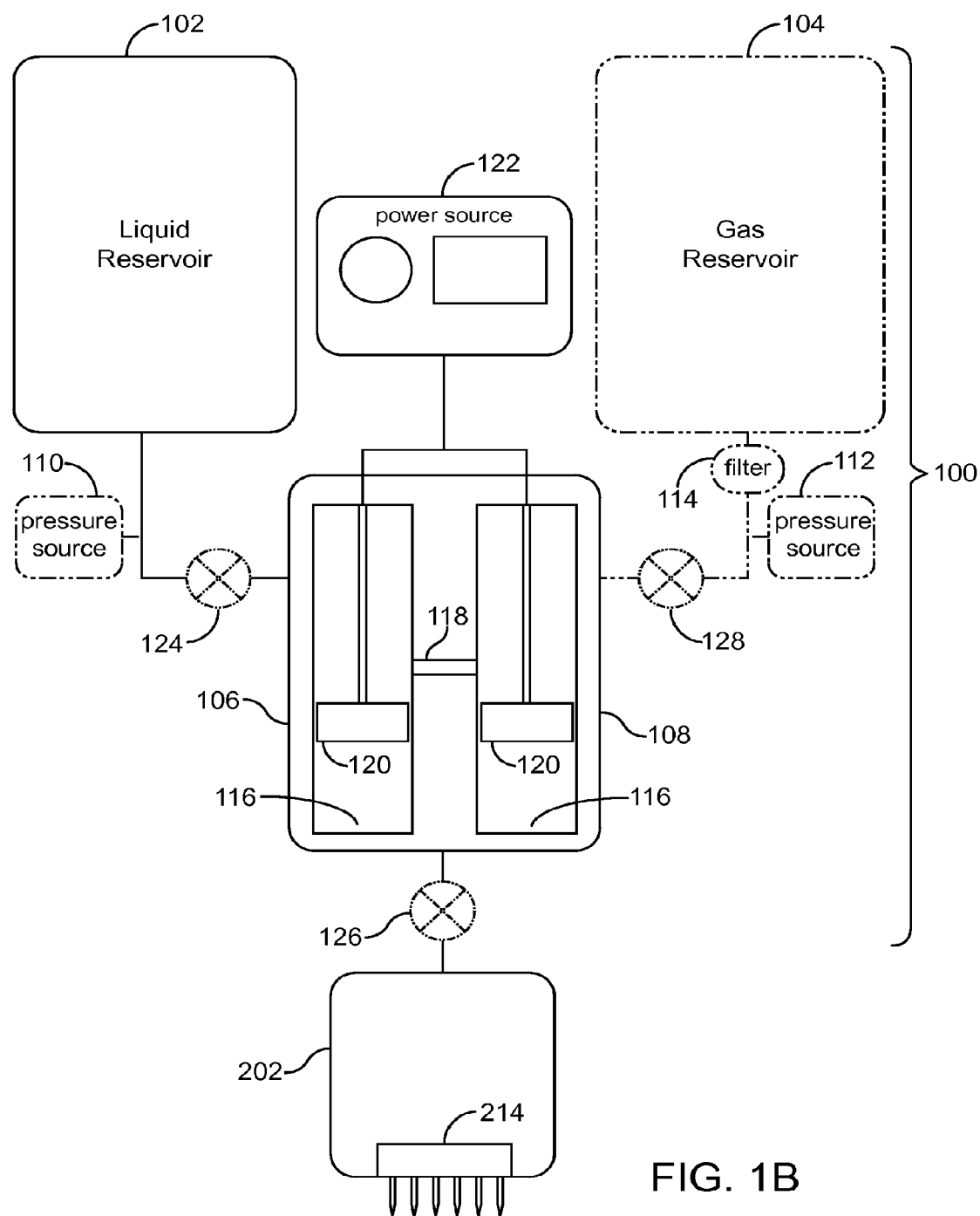

FIG. 1B is a more detailed illustration of a first embodiment of the bubble generator 106 and includes a housing 108, a pair of cylinders 116 interconnected by a pathway 118. At least one of the cylinders 116 is in fluid communication with the liquid reservoir 102, and at least one of the cylinders 116 is in fluid communication with the gas reservoir 104 (which may be ambient environment). The fluid pathway 118 provides fluid communication between the cylinders 116.

One or more of the cylinder(s) 116 may be provided with a reciprocating piston 120 driven by an external power source 122 such as a source of compressed air, spring, elastomeric member, motor, stepper motor or the like. According to one embodiment, the reciprocating piston 120 is a pneumatic piston manufactured by the Bimba Corporation.

Liquid from the liquid reservoir 102 may be pushed into the bubble generator 106 under positive pressure from an external pressurization source 110 (shown in dashed lines); it can be drawn into the bubble generator 106 under partial pressure which may for example be generated by the reciprocating piston 120; or it can flow into the generator 106 under gravity. Similarly, gas from the gas reservoir 104 may be pushed into the bubble generator 106 under positive pressure from an external pressurization source 112 (shown in dashed lines) or it can be drawn into the bubble generator 106 under partial pressure. As will be described below, the piston 120 may also serve a dual purpose as a fluid pressurization mechanism for injecting the fluid into the tissue.

The bubble generator 106 may or may not be pressurized to enhance the saturation of the gas in the solution or prevent dissolved gas from coming out of solution. An optional fluid pressurization mechanism 110 (shown in dashed lines) may be used to maintain the fluid at a desired pressurization. As will be described in further detail below, the fluid may be chilled to further enhance solubility/saturation of the gas in the solution.

Figure 1C:
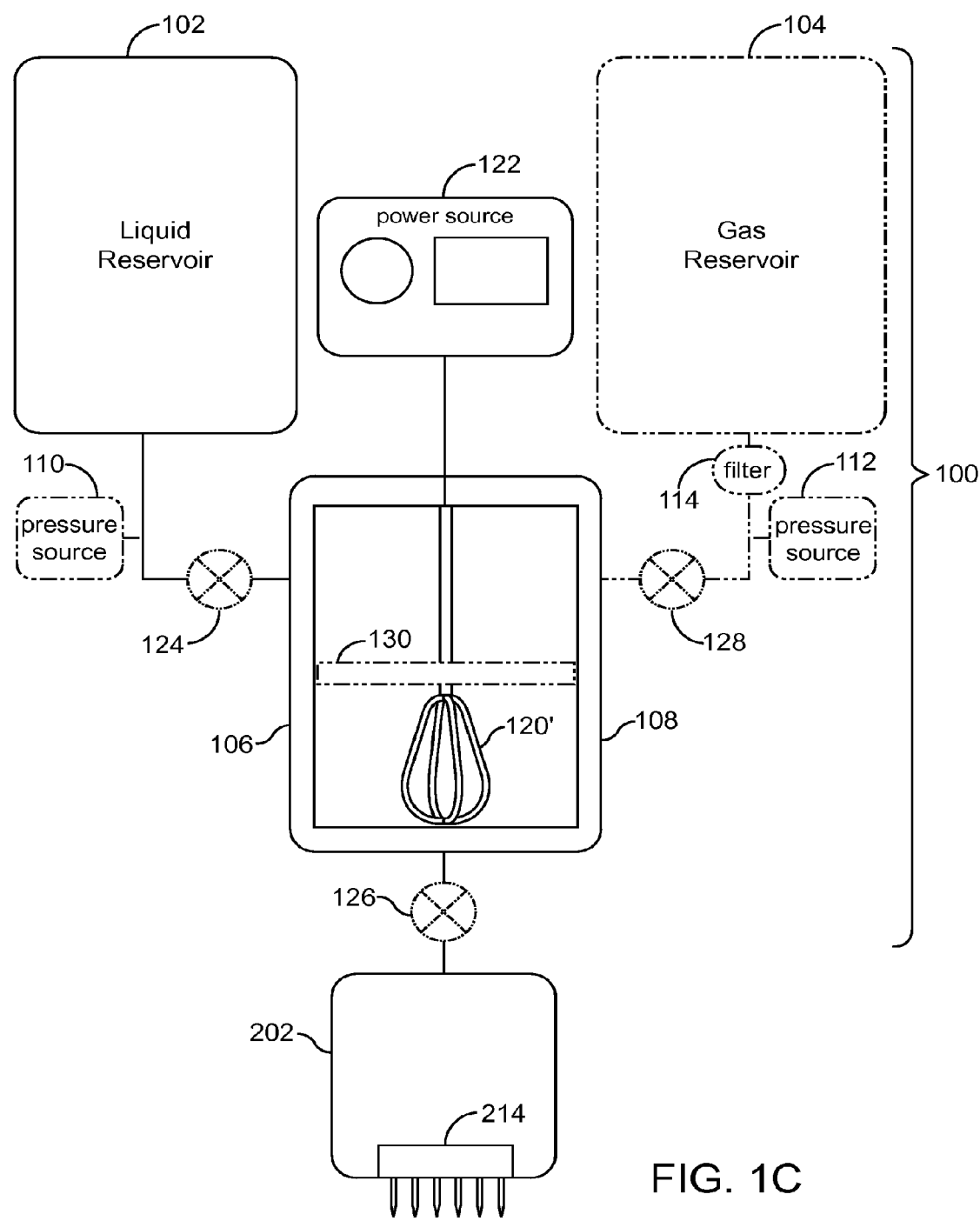
FIG. 1C is a block diagram of a first modification of the bubble generator of FIG. 1B.

FIG. 1C is an alternate embodiment of the microbubble generator 106, which utilizes a member 120' (rotor) such as a blade, paddle, whisk, semi-permeable membrane or the like driven by an external power source 122 to generate the microbubbles within a cylinder or mixing chamber (stator) 116. As will be appreciated by one of ordinary skill in the art the member 120' is rotationally driven by the external power source 122 within a cylinder 116 or the like. An optional fluid pressurization mechanism 130 may be used for injecting the fluid into the tissue.

The fluid in the reservoir 102 may be at ambient temperature. Alternatively, the fluid may be chilled slightly to enhance gas solubility (super saturation). The fluid reservoir 102 may be thermally insulated to maintain the fluid at its present temperature and/or the fluid reservoir 102 may include a heating/cooling mechanism (not illustrated) to maintain the fluid at a predetermined temperature.

If the gas used is air then the gas reservoir 104 may be eliminated in favor of simply drawing air from the environment, i.e., the room housing the device 100 ("room air"). If room air is used, the device 100 may include an air filter 114 (shown in dashed lines) such as a HEPA filter or the like.

Figure 1D:
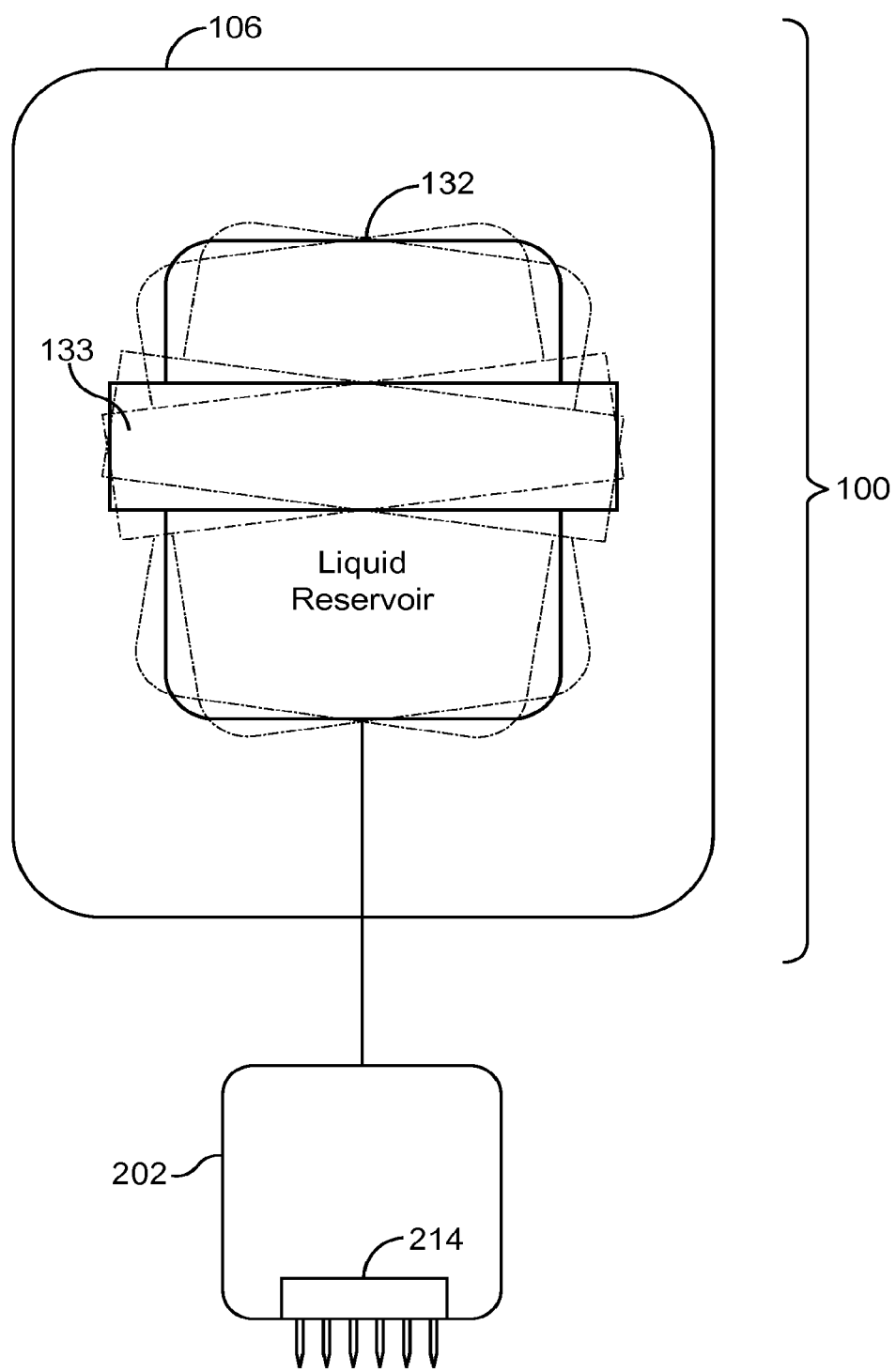
FIG. 1D is a block diagram of a second modification of the bubble generator of FIG. 1B.
Figure 2:
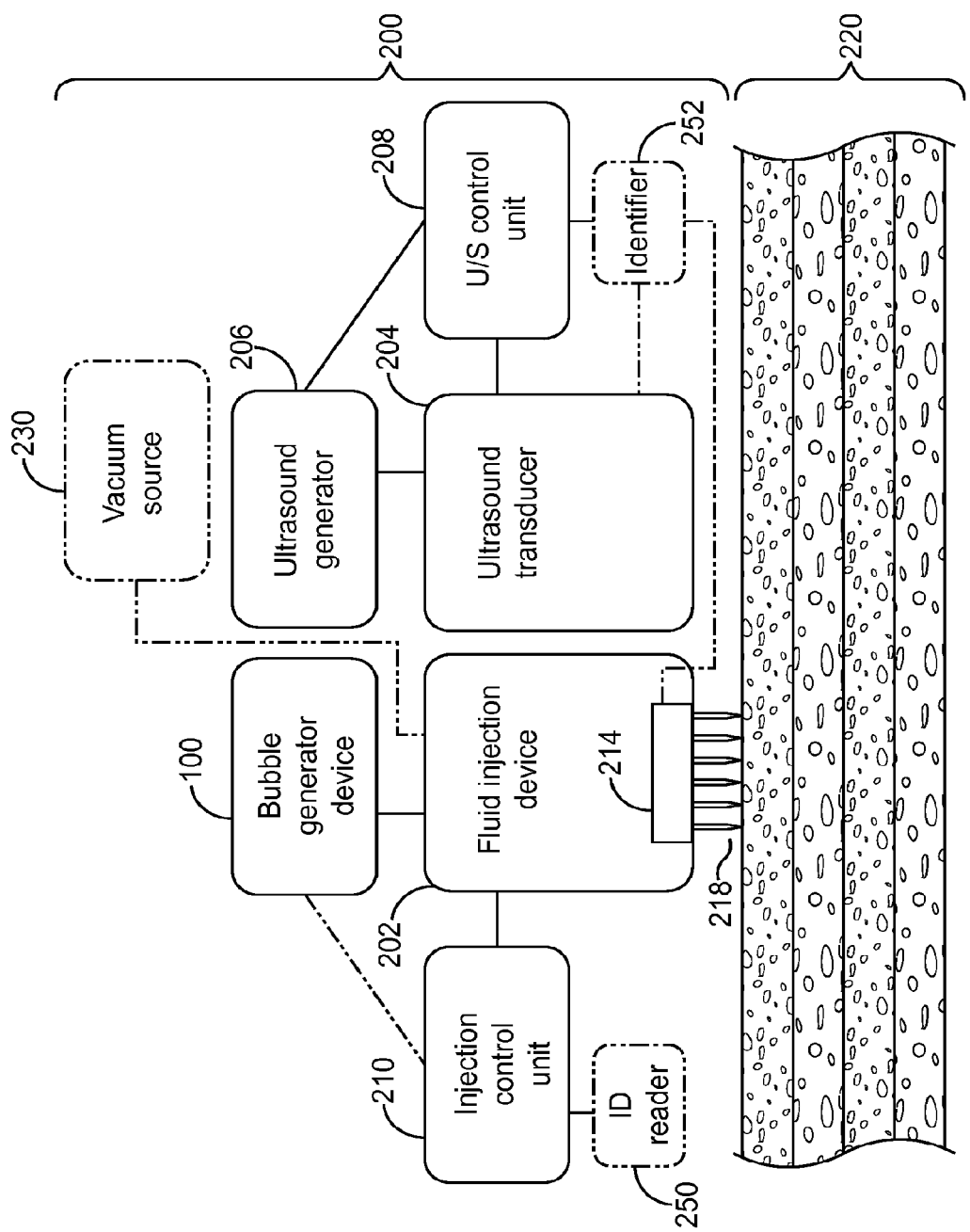
FIG. 2 is a block diagram of a tissue cavitation system according to the present invention.

FIG. 1D is an alternate embodiment of the microbubble generator 106, which utilizes an agitator 133 to agitate or shake a container or cartridge 132 containing measured amounts of liquid and gas and generate the microbubbles within the cartridge 132. The microbubble solution is dispensed from the cartridge 132 to fluid injection device 202 (FIG. 2). Additionally, this cartridge 132 may incorporate an active heating/cooling mechanism to control the temperature of the fluid at a predetermined setting. Furthermore, the cartridge 132 may be pressurized, such as by compressed air or mechanical mechanism to allow dispensation of the contents at a predetermined rate and pressure.

FIG. 2 is a block diagram of a liposculpture system 200 according to the present invention. The system 200 includes device 100, a fluid injection device 202, an ultrasound transducer apparatus 204, an ultrasound generator 206, an ultrasound control unit 208, and an injection control unit 210. Device 100 may include the bubble generator 106 depicted in FIGS. 1A-1D or may be one of the alternative embodiments disclosed herein below.

The fluid injection device 202 may include a needle array 214 which may include one or more needles 218. Alternatively, the fluid injection device 202 may, for example, include one or more hypodermic syringes.

The fluid injection device 202 further includes or is operably connected to a fluid pressurization mechanism 110 for pushing the solution into the tissue. As noted above, the piston 120 or the like used to express fluid between the cylinders 116 may serve as the fluid pressurization mechanism 210.

One or more of the components collectively termed system 200 may be combined. For example the fluid injection device 202 may be integrated as a single component with the ultrasound transducer apparatus 204 and/or the fluid injection control unit 210. Likewise, the ultrasound control unit 208 can be integrated as a single component with the ultrasound generator 206. Such integration of components is contemplated and falls within the scope of the present invention.

The fluid injection control unit 210 may control the amount of fluid and gas dispensed into the bubble generator 106 and/or the amount of solution injected into the tissue. Optionally, the control unit 210 may be interfaced directly or indirectly with the fluid metering device(s) 124, 126 and the gas metering device 128. The fluid injection control unit 210 may control the mixing or agitation (if any) of the solution within the bubble generator 106. The fluid injection control unit 210 may control the injection of solution into the tissue 220 by the injection device 202, including the deployment of a needle array 214, the depth to which the needle array 214 is deployed, and the amount of solution injected.

The fluid injection control unit 210 may control the individual deployment and retraction of one more needles (or hypodermic syringes) of the needle array 214. Thus, the control unit 210 may deploy or retract the needles 218 (or hypodermic syringes) one at a time, may deploy or retract two or more needles 218 at a time, or may deploy or retract all of the needles simultaneously.

Additionally, the fluid injection control unit 210 may individually control the amount of solution delivered to each needle 218. One of ordinary skill in the art will appreciate that there are many ways to control the amount of solution delivered to each needle 218. For example, it may be desirable to deliver more solution in the center of the treatment area and less to the peripheral portion of the treatment area or vice-versa.

If the injection device 202 utilizes hypodermic syringes, then the fluid injection control unit 210 may control the amount of fluid distributed to each syringe. As noted above it may be desirable to provide differing amounts of solution to different areas of the treatment area, and this may be achieved by varying the amount of solution in each syringe.

Figure 3A:
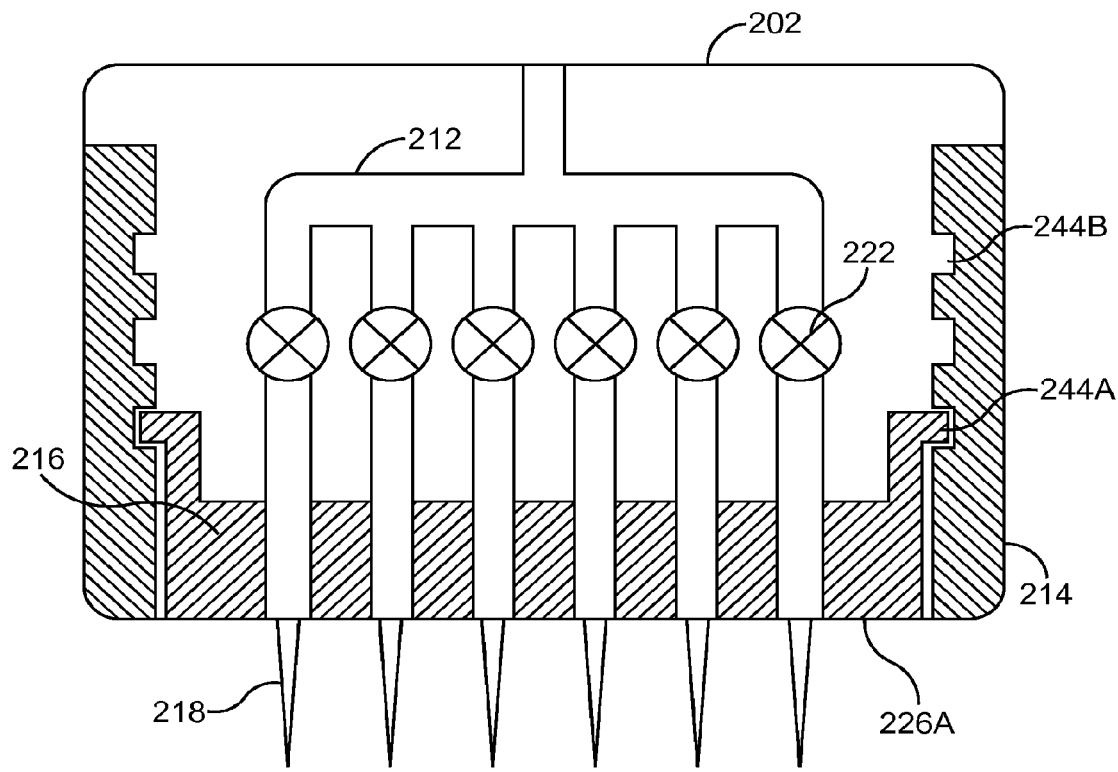
FIGS. 3A-3C are views of a fluid injection device including a manifold and an injection depth adjustment mechanism according to the present invention.
Figure 3B:
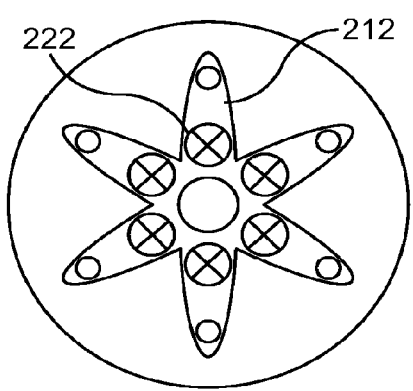
Figure 3C:
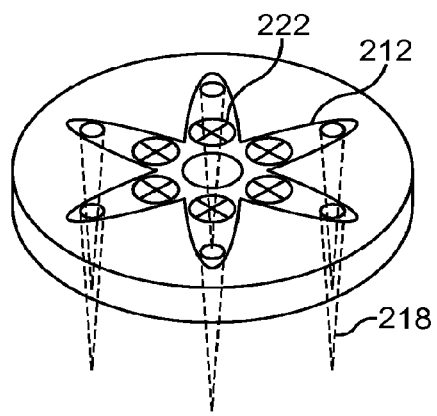

As best seen in FIGS. 3A-3C, the fluid injection device 202 may include a manifold or fluid distribution pathway 212 (shown in dashed lines) in fluid connection with device 100 and needle array 214, and a needle deployment mechanism 216 operably connected to the needle array 214. The manifold 212 is the fluid pathway used to transport the micro bubble solution from the micro bubble generator 106 to the needle array 214.

One or more flow control devices 222 may be provided in the fluid pathway 212 to enable individualized control of the amount of fluid dispensed to each of the needles or syringes 218. The manifold 212 alone or in combination with the flow control devices 222 controls the distribution of the micro bubble solution among the needles 218. The manifold 212 may be configured to deliver a uniform amount of solution to each of the needles 218 (or hypodermic syringes), or it may be configured to deliver differing amounts of solution to different needles 218. The flow control devices 222 may be manually adjustable and/or may be controlled by the injection control unit 210. An alternate embodiment may include infinitely variable volume control at each needle or hypodermic through active means, such as with an electronic flow meter and controller.

It may be desirable to deploy all of the needles 218 simultaneously into the tissue but deliver solution to one or more needles 218 individually. For example, it may be desirable to deliver solution sequentially to groups of one or more needles 218. If needles 218 are deployed individually or in groups of two or more it may be desirable to deliver solution only to the deployed needles 218.

As will be explained below, the injection depth may be manually determined by selecting an appropriate needle length or setting a desired injection depth.

The needle deployment mechanism 216 (FIGS. 2 and 3A) deploys one or more needles 218 (or hypodermic syringes) of the needle array 214 such that needles 218 penetrate a desired distance into the tissue. The needle deployment mechanism 216 may be configured to deploy the needle(s) 218 to a fixed predetermined depth or may include means for adjusting the depth that the needle(s) 218 are deployed.

There are several broad approaches for adjusting the injection depth which may be utilized. One way to adjust the injection depth is to provide needle arrays 214 of varying length needles. According to this embodiment, the user simply selects an array 214 having shorter/longer needles 218 to achieve a desired injection depth. Moreover, the different length needles 218 may be used within a given array 214.

According to another approach, the needle array 214 is displaced vertically in order to adjust the injection depth.

FIG. 3A shows aspects of an adjusting means, which may include a flange 244A and a groove 244B arrangement for vertically adjusting the needle array in discrete intervals.

Figure 3D:
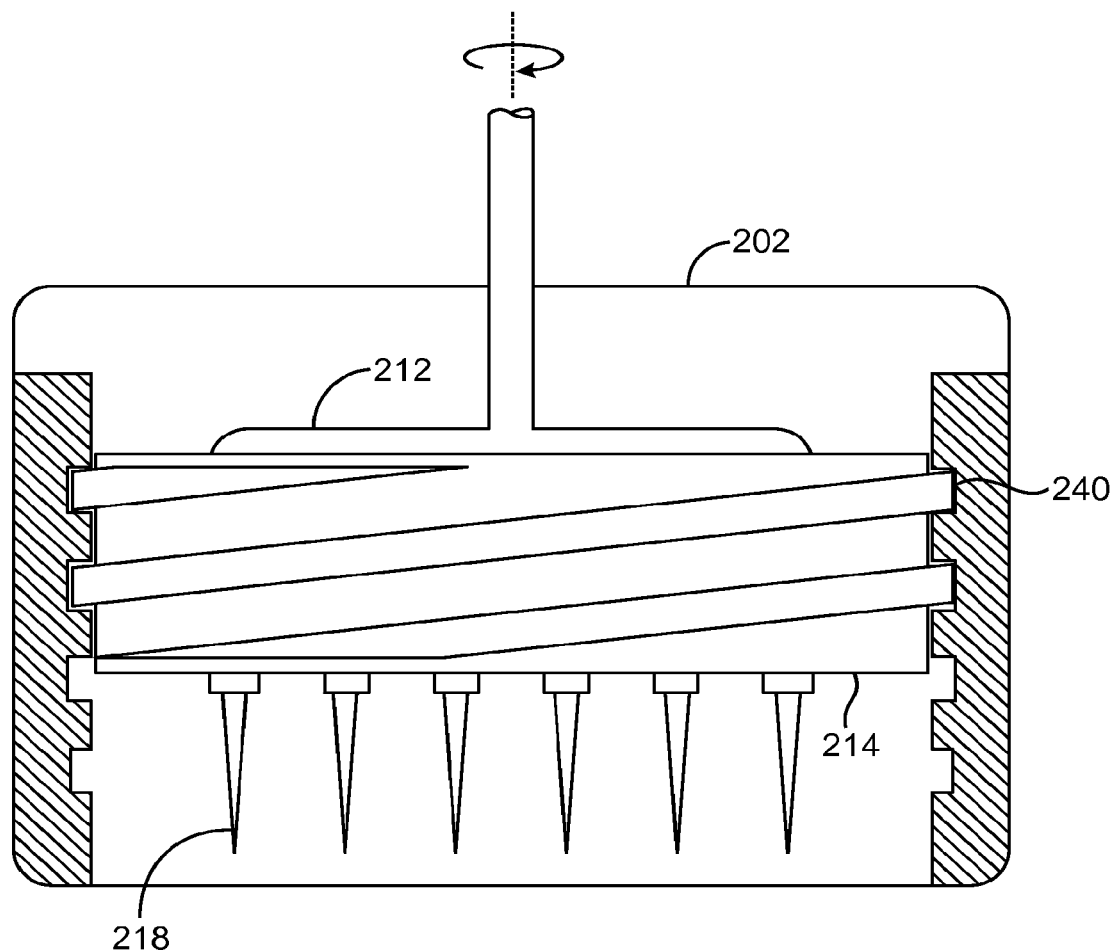
FIG. 3D shows a modified mechanism for adjusting the injection depth of the fluid injection device of FIG. 3A.

FIG. 3D shows aspects of an adjusting means, which may include mating screw threads 240 formed on the needle array 214 and the fluid injection device 202 or housing 108 which enable the user to vertically adjust the needle array 214 thereby altering the injection depth.

According to one embodiment, the injection depth may be continuously adjusted within a given range of injection depths. For example, the user may be able to continually adjust the injection depth between 5 and 12 millimeters by rotating the needle array 214. According to an alternate embodiment, the injection depth may be adjusted in discrete intervals. For example, the user may be able to adjust the injection depth between 3 and 15 millimeters in 1 millimeter increments. In yet another embodiment, the needle depth may be controlled electronically whereby the user enters a specified depth on the control unit 210.

The injection depth adjustment described above may specify the injection depth for the entire needle array 214. However, according to yet another approach it may be desirable to facilitate the individualized adjustment of one or more needles 218 of the needle array 214. The needle deployment mechanism 216 may allow for the independent adjustment of the injection depth for one or more of the needles 218 or syringes.

One or more of the needles 218 or syringes may be displaced vertically in order to adjust the injection depth of individual needles. The adjustment of the injection depth (vertical needle displacement) may be continuous or in discrete intervals, and may be manual or may be adjusted via the injection control unit 210.

Figure 4A:
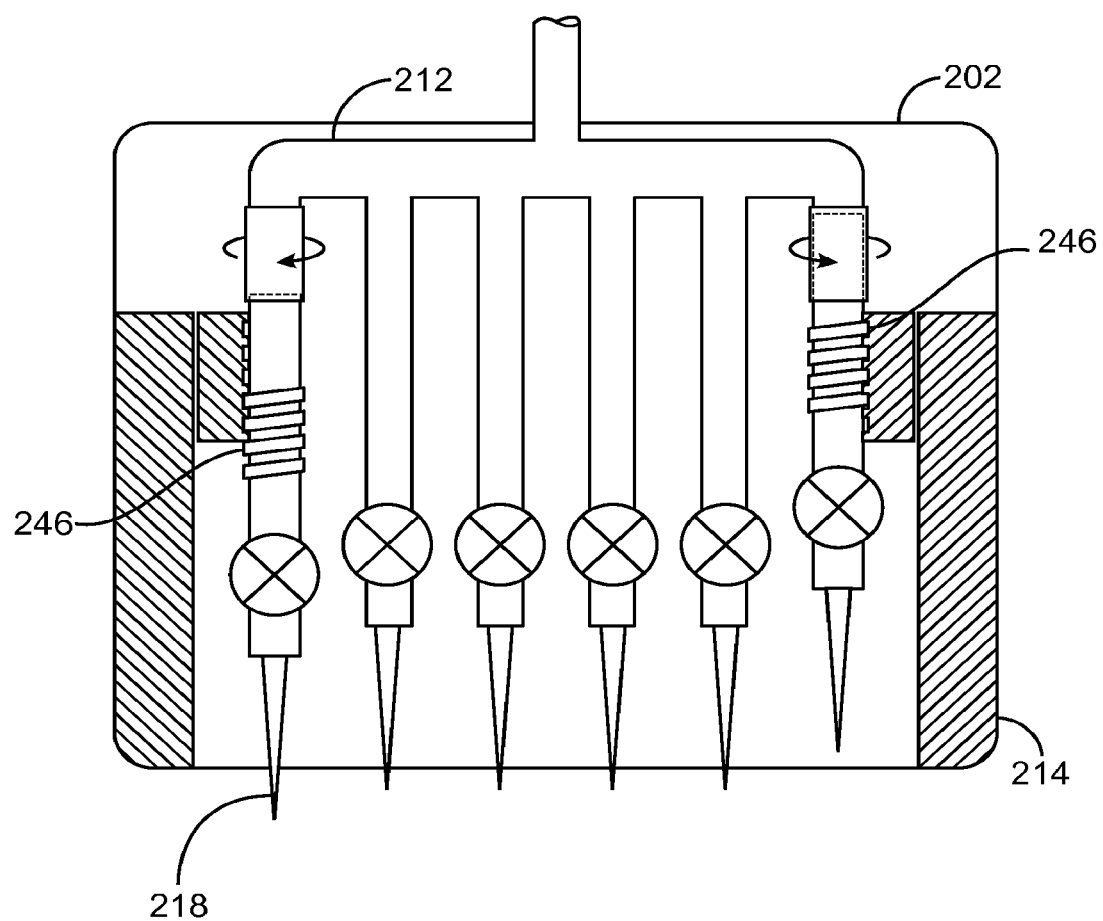
FIGS. 4A-4C show an alternate embodiment fluid injection device including a mechanism for individually adjusting the fluid flow through each needle and a mechanism for individually adjusting the injection depth.

As noted above, the injection depth may be adjusted by providing mating screw threads 246 to dial in the desired injection depth (FIG. 4A), a standoff 248 to provide a means for adjusting the injection depth in discrete intervals (FIG.

4B), or the like on the needle array 214 to adjust the vertical height of the needles 218 relative to the tissue apposition surface 226A.

Figure 4B:
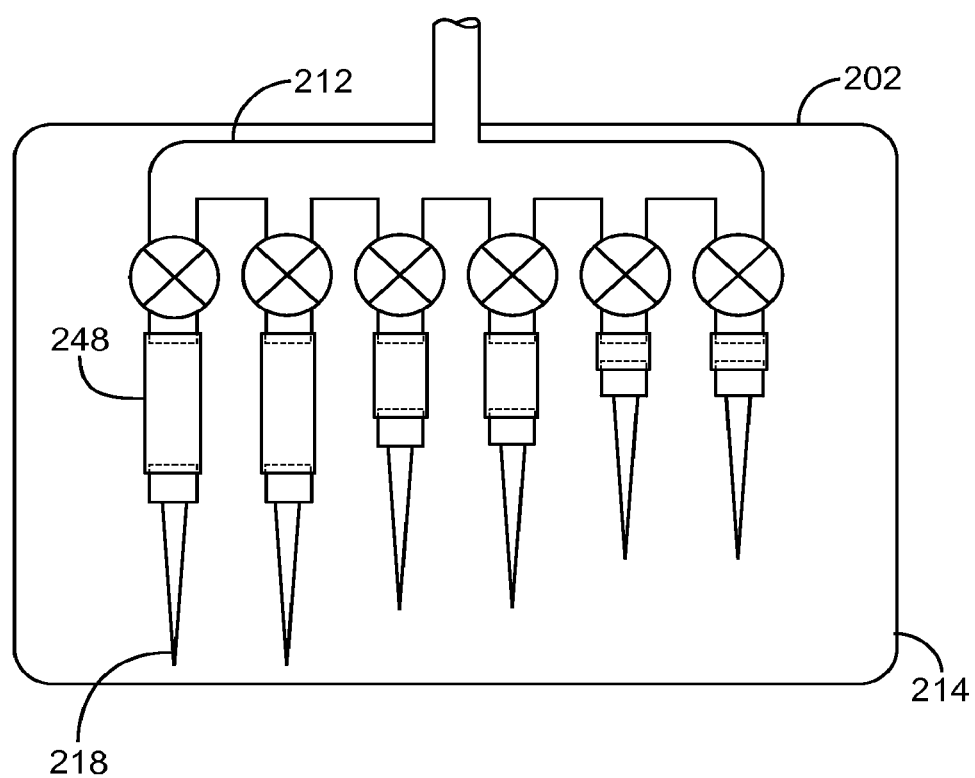
Figure 4C:
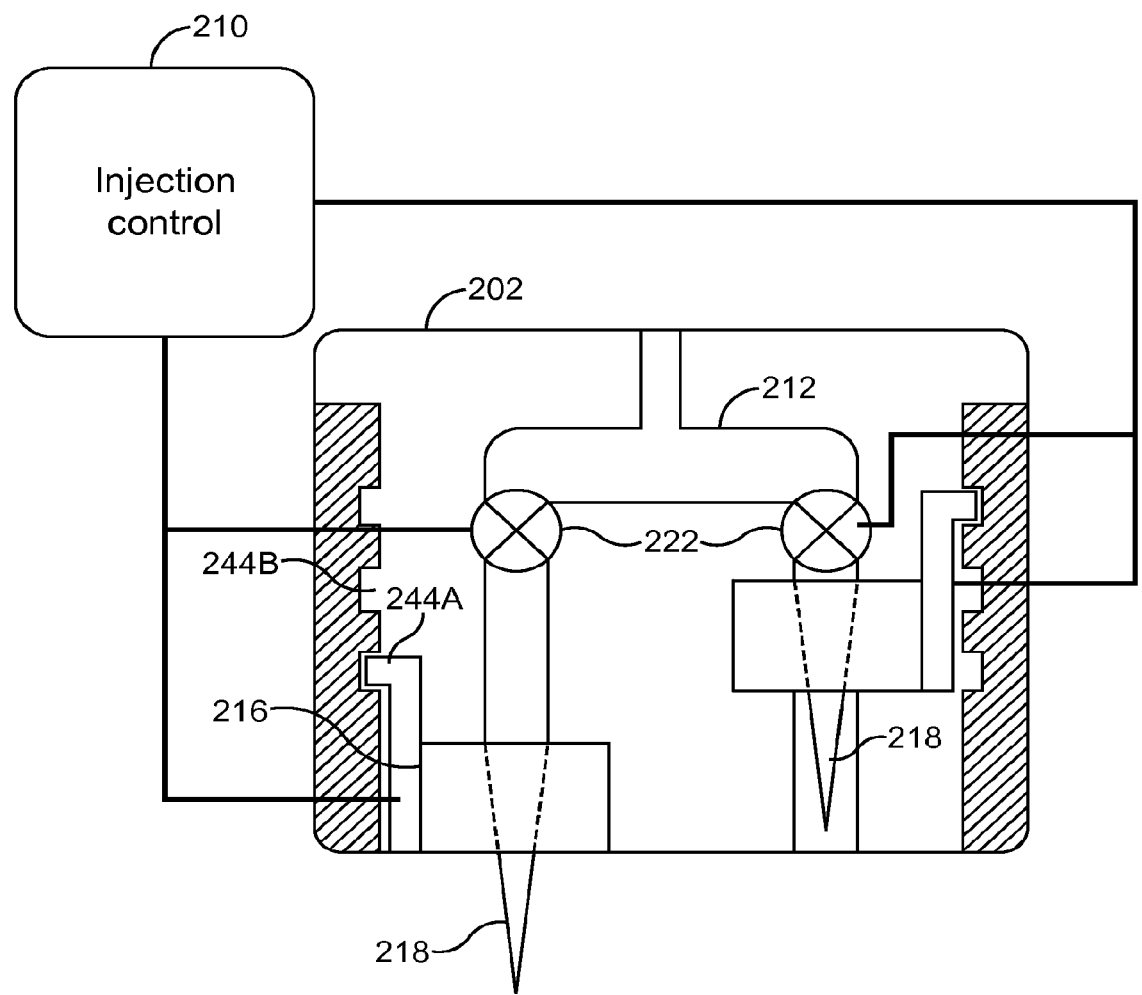

Yet another approach to individualized injection depth control is to deploy individual needles or syringes 218 as opposed to deploying the entire needle array 214. The injection control unit 210 or needle deployment mechanism 216 selects the injection depth of each individual needle or syringe 218 (FIG. 4C).

One of ordinary skill in the art will appreciate that there are many other ways to implement the adjustment of the injection depth. The invention is not limited to the embodiments depicted in the drawings.

The needle deployment mechanism 216 deploys the needles 218 in response to a signal from the fluid injection control unit 210. The deployment mechanism 216 may include a spring, pneumatic ram, or the like which deploys the needles 218 with sufficient force to penetrate the tissue 220. The fluid injection control unit 210 synchronizes the deployment mechanism 216 with the injection of the micro bubble solution into the tissue.

A predetermined amount of the solution may be injected at a single injection depth. Alternatively, the fluid injection control unit 210 in synchronism with the deployment mechanism 216 may inject solution at each of plural injection depths, or may inject continuously as the needle array 214 on either the forward (penetration) or rearward (withdrawal) strokes. It may be desirable to deploy the needles to a first depth within the tissue and then retract the needles to a slightly shallower injection depth before injecting the solution.

Figure 5:
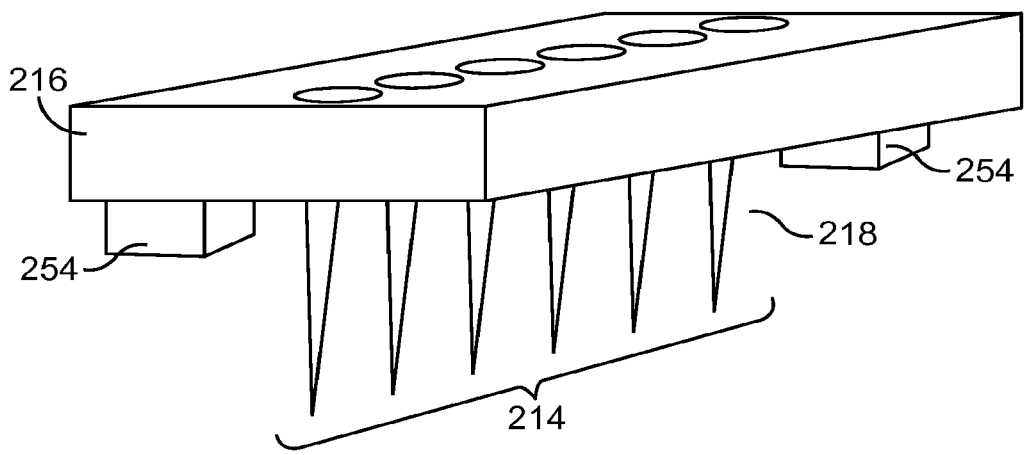
FIG. 5 shows a needle array including an optional sensor used in a fluid injection device according to the present invention.

FIG. 5 is an enlarged view of the needle array 214 including at least one hypodermic needle or micro-needle 218. The invention is not limited to any particular length or gauge needle, and needles 218 are selected in accordance with the depth of the tissue to be treated and to accommodate patient comfort. Moreover, it may be desirable for the needle array 214 to include needles of varying length and/or needles of varying gauge.

The embodiment depicted in FIG. 5 includes a plurality of uniformly spaced needles 218. However, the scope of the invention is not limited to any particular number of needles 218; moreover, the invention is not limited to any particular geometric arrangement or configuration of needles 218. It may be desirable to have non-uniform needle spacing. For example, it may be desirable to have a smaller (denser) needle spacing in one portion of the treatment region and a greater (sparser) needle spacing in another portion. The use of additional needles 218 may facilitate uniform distribution of the microbubble solution in the tissue 220 and/or reduce the number of distinct injection cycles needed to treat a given area.

Figure 6A:
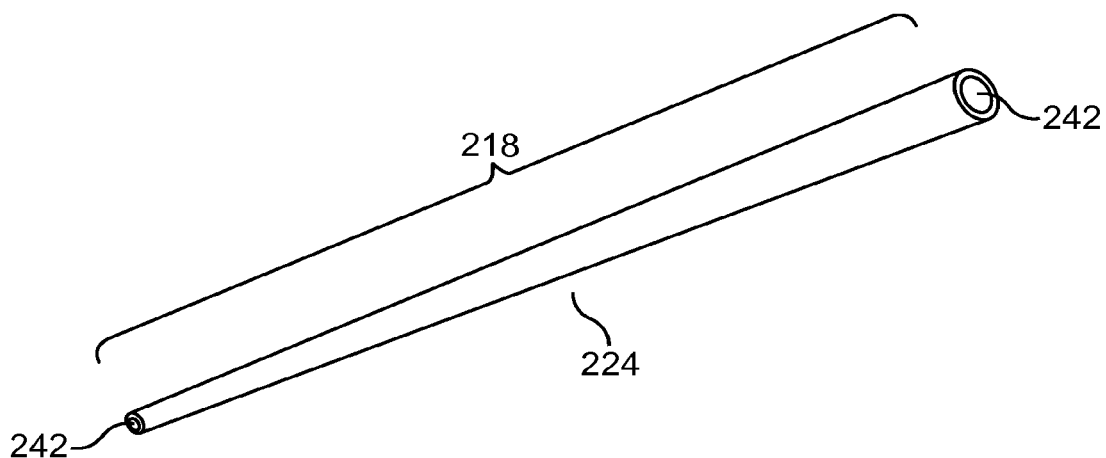
FIGS. 6A and 6B show straight and side firing needles used in the needle array of FIG. 5.

FIG. 6A depicts a needle 218 having a single injection orifice 242, which is linearly aligned with the needle shaft 224. The hypodermic needle 218 is a tubular member having a lumen configured for injection of the solution through the needle and into the tissue. The lumen may include a textured surface for promoting the generation of micro bubbles.

Figure 6B:
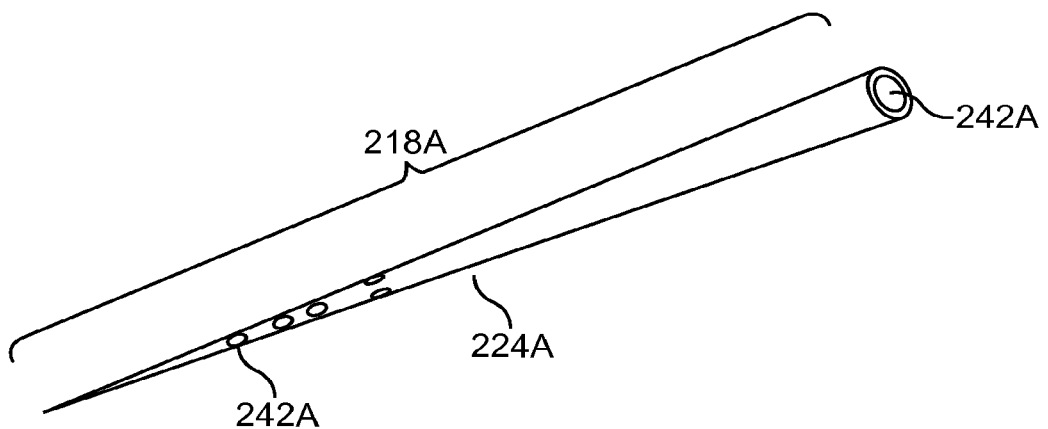

FIG. 6B depicts an alternative needle 218A having one or more side firing orifice(s) 242A which are generally orthogonal to longitudinal axis of the shaft 224A. The side firing orifice(s) may be formed at different heights along the length of the needle shaft such that solution is injected at varying injection depths. These orifice(s) may also be arranged in a specific radial pattern to preferentially direct the flow distribution.

Depending on the characteristics of the tissue undergoing treatment the user may find that needle 218 is preferable over needle 218A or vice versa. Reference to the needles 218 should be understood to refer generally to both the needles 218 (FIG. 6A) and the needles 218A (FIG. 6B).

Figure 7:
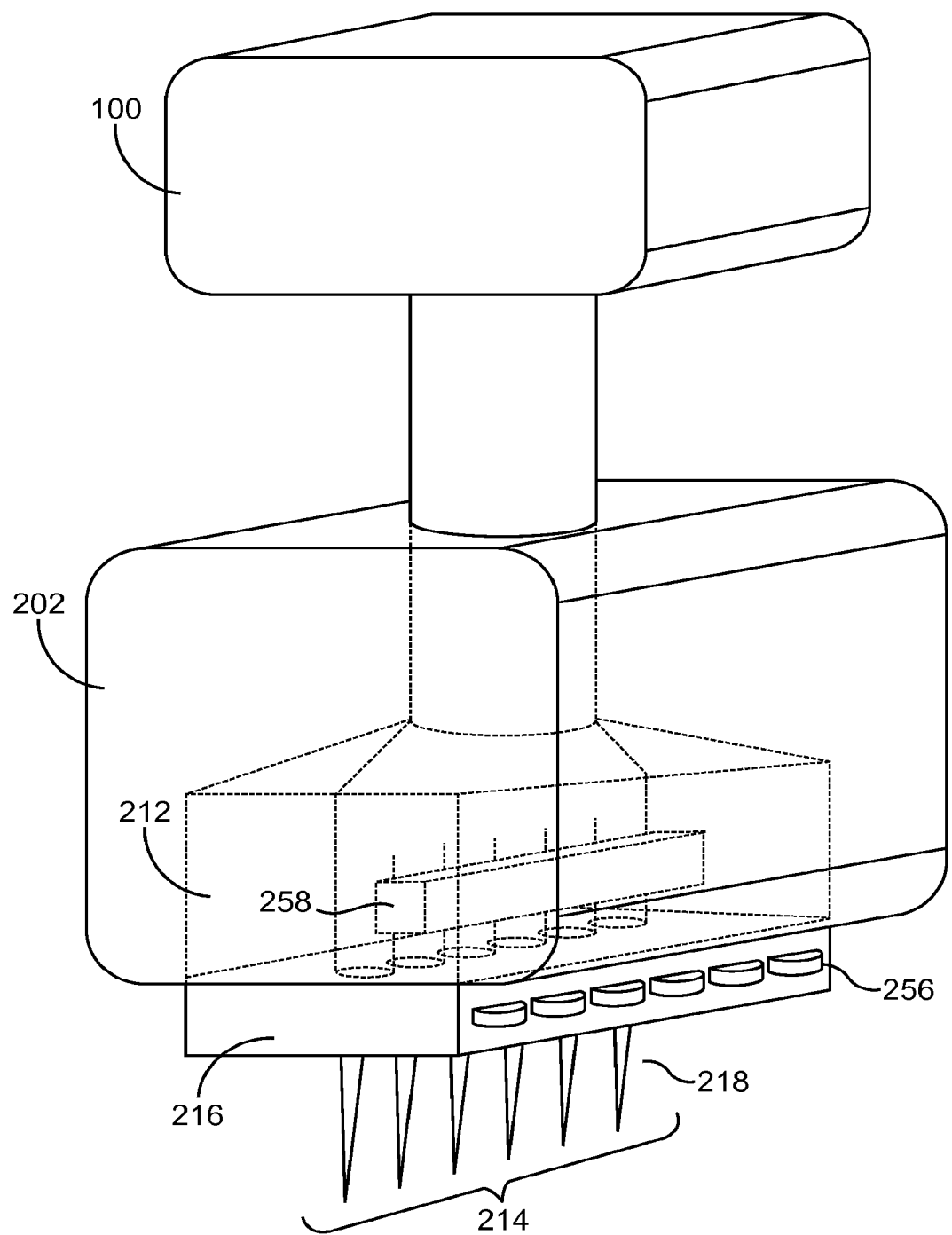
FIG. 7 is a block diagram a fluid injection device including a mechanism for rotating the needle in situ.

As shown in FIG. 7, some embodiments of the invention may include a mechanism 256 for selectively rotating one or more of the needles 218 in situ. This feature may facilitate the uniform distribution of solution in the tissue.

According to some embodiments of the invention it may be desirable for the needle deployment mechanism 216 to ultrasonically vibrate one or more of the needles 218. This feature may facilitate tissue penetration and/or bringing dissolved gas out of solution. For example, an ultrasound transducer 258 may be operably coupled to the needles 218 and/or the needle array 214. The ultrasound transducer 258 is shown for the sake of convenience in FIG. 7 however, the transducer 258 may be used in a device which does not include the needle rotation mechanism 256 and vice versa.

As best seen in FIG. 8A, the hypodermic needle 218 has a proximal end connected to the fluid distribution pathway 212 and a distal end configured for penetrating into the tissue 220 to be treated. In one embodiment, the needles 218 may include micro-needles.

Figure 8B:
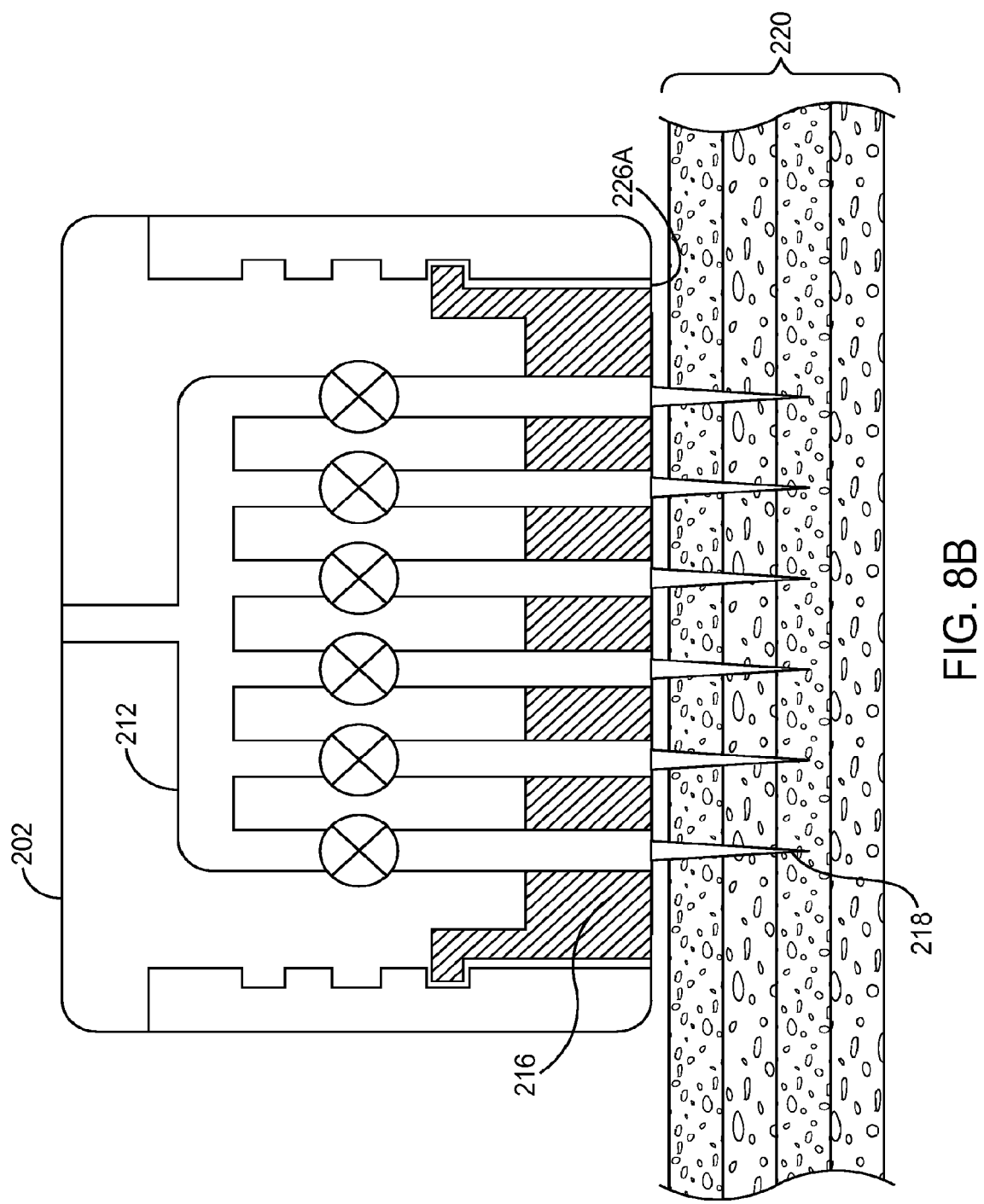

In one embodiment, the fluid injection device 202 includes needle deployment mechanism 216 for moving the hypodermic needle 218 from a fully retracted position (FIG. 8A) in which the distal end of the needle 218 is housed inside the solution injection member 202 to a fully extended position (FIG. 8B).

Figure 9A:
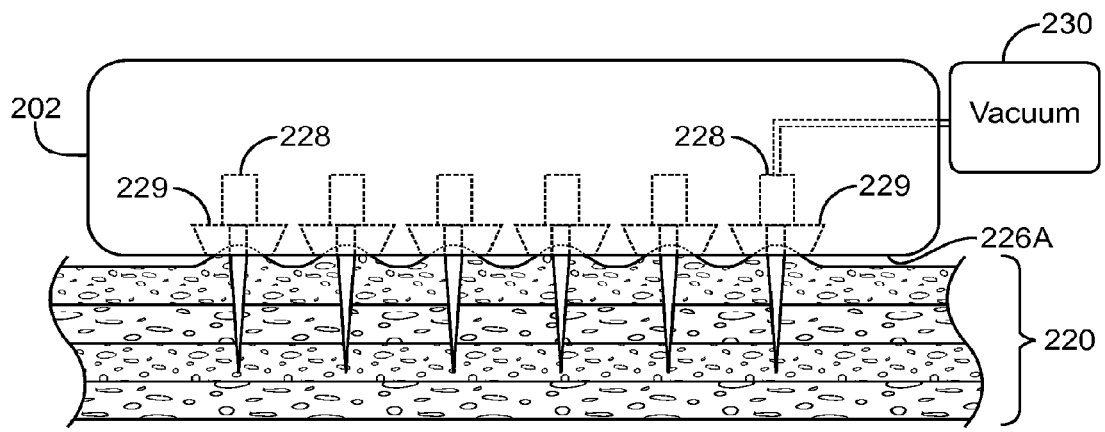
FIGS. 9A-9C show a tissue apposition mechanism according to the present invention.
Figure 9B:
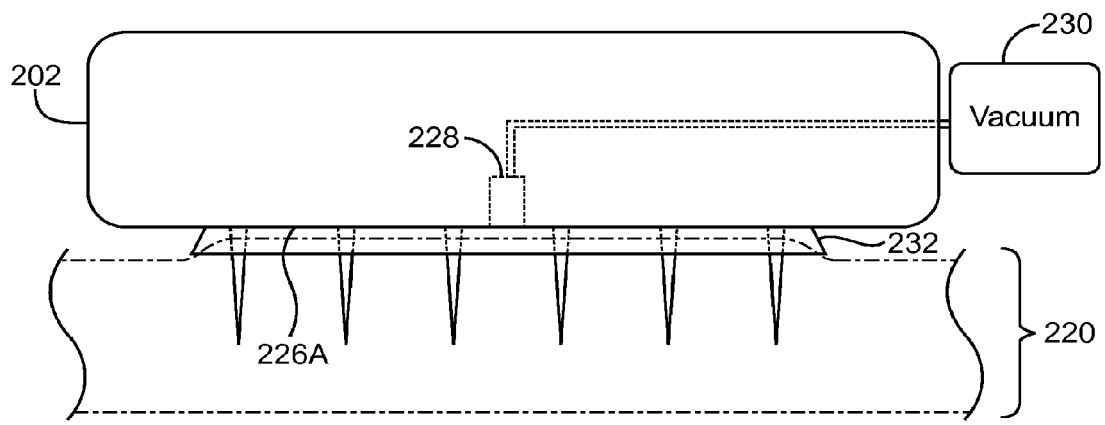
Figure 9C:
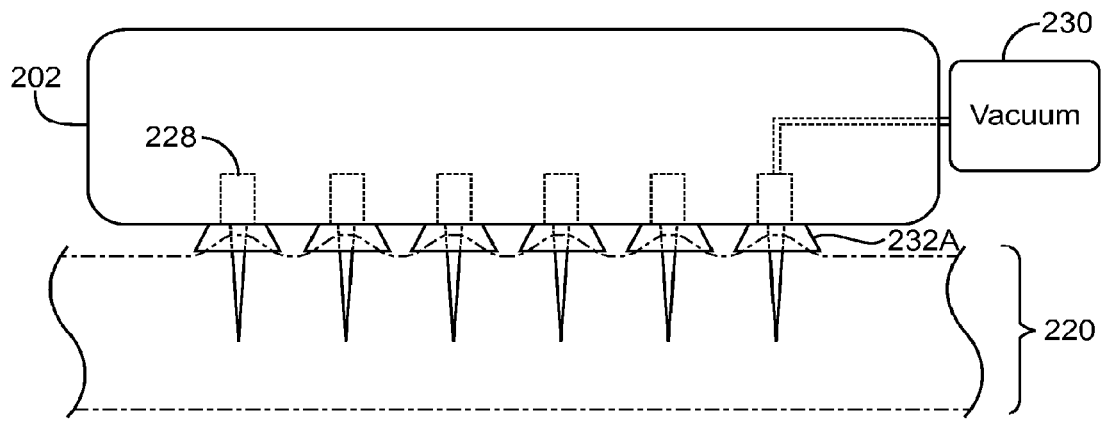

As shown in FIGS. 9A-9C, the fluid injection device 202 may optionally be provided with a tissue apposition mechanism which urges the device 202 into firm apposition with the tissue 220 undergoing treatment. According to one embodiment the tissue apposition mechanism includes at least one vacuum port 228 and a vacuum source 230 in fluid communication with the vacuum port 228. The vacuum port 228 may be defined in the needle array 214 and/or the housing 108. In operation the tissue apposition surface 226A is pulled into apposition with the tissue 220 when vacuum from the vacuum source 230 is transmitted through the vacuum port 228 to the tissue 220.

In some embodiments it may be desirable to provide a one-to-one relationship between needles 218 and vacuum ports 228. Moreover, the needle(s) 218 may be positioned within the vacuum port(s) 228. The vacuum port 228 may define a recess or receptacle 229 such that the tissue 220 is at least partially pulled (sucked) into the recess 229 by the vacuum force. Moreover, the needles 218 may be at least partially housed within and deployed through the recess 229.

An optional flange 232 (show in dashed lines) may surround (skirt) the periphery of the needles 218 (or 218A) to channel/contain the suction force. Alternatively, a separate flange 232A may surround (skirt) each of the needles 218 (or 218A) to channel/contain the suction force.

It may be desirable to have one or more vacuum ports 228 spaced along a periphery of the apposition surface 226A. Moreover, it may be desirable to include a central portion apposition surface 226A, which does not include any vacuum ports 228 (no suction zone). Alternatively, it may be desirable to have vacuum ports confined to a central portion of the apposition surface 226A.

It should be appreciated that the liquid reservoir 102 and gas reservoir 104, in each of the aforementioned embodiments may be replaced with a cartridge 132 (FIG. 1D) containing a pre-measured amount of liquid and gas. The gas may be fully or partially dissolved in the fluid. In its simplest form the cartridge 132 is simply a sealed container filled with a predetermined amount of gas and liquid, e.g., a soda can.

Figure 10A:
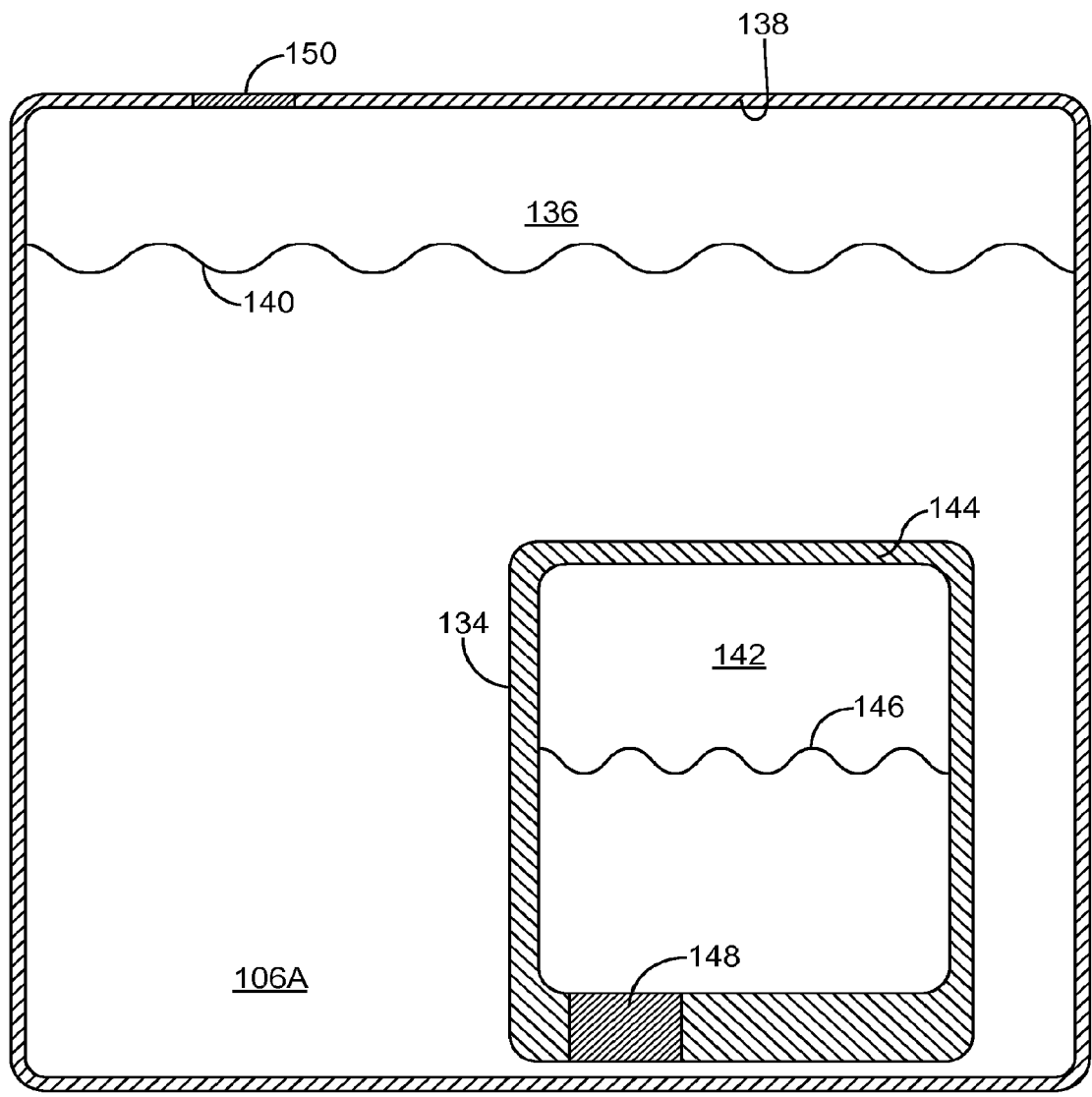
FIGS. 10A and 10B show an alternate embodiment bubble generator and a system for injecting and insonating bubbles using the same.

FIG. 10A shows an enhanced cartridge 106A ("Guinness can"), which may be used to replace the liquid reservoir 102, gas reservoir 104, and bubble generator 106 in each of the aforementioned embodiments. In this embodiment, the cartridge 106A includes a hollow pressurized pod 134 such as disclosed in U.S. Pat. No. 4,832,968, which is hereby incorporated by reference. Both the cartridge 106A and the pod 134 contain a solution of gas and liquid under greater than ambient pressure which may for example be achieved by providing or introducing a dose of liquid nitrogen into the solution before sealing the cartridge 106A.

The cartridge 106A includes a headspace 136, which is bounded between a top inner surface 138 and a gas-liquid interface 140. The pod 134 includes a similar headspace 142, which is bounded between a top inner surface 144 and a gas-liquid interface 146.

The pod 134 includes a small opening or orifice 148, which enables the pressure within the headspace 136 of the cartridge 106A to reach equilibrium with the pressure within the headspace 142 of the pod 134. When a seal 150 of the cartridge 106A is pierced the pressure within the headspace 136 rapidly reaches equilibrium with the ambient pressure. In the moments after seal 150 is pierced the pressure within the pod 134 is greater than the pressure in the headspace 136 of the cartridge 106A because the orifice 148 restricts the rate of flow of solution out of the pod 134. A jet of solution forcefully streams out of the orifice 148 into the solution within the cartridge 106A, which agitates and/or shears the solution within the cartridge causing some of the dissolved bubbles to come out of solution thereby generating microbubbles in the solution.

The pod 134 is preferably situated at or near the bottom of the cartridge 106A such that the orifice 148 is maintained below the liquid gas interface 140.

Figure 10B:
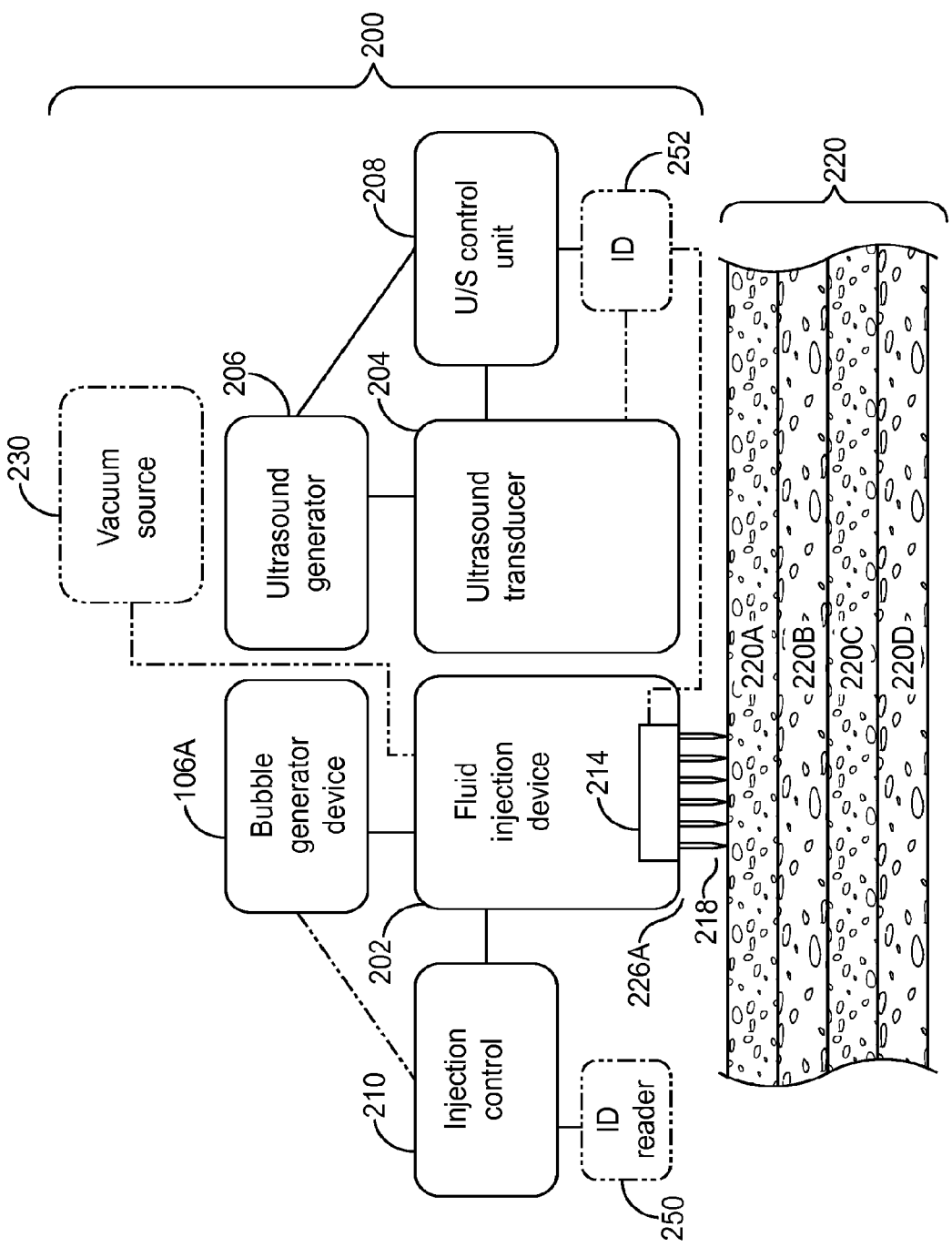

FIG. 10B is a block diagram showing the system 200 including cartridge 106A in place of bubble generator 106.

Figure 11:
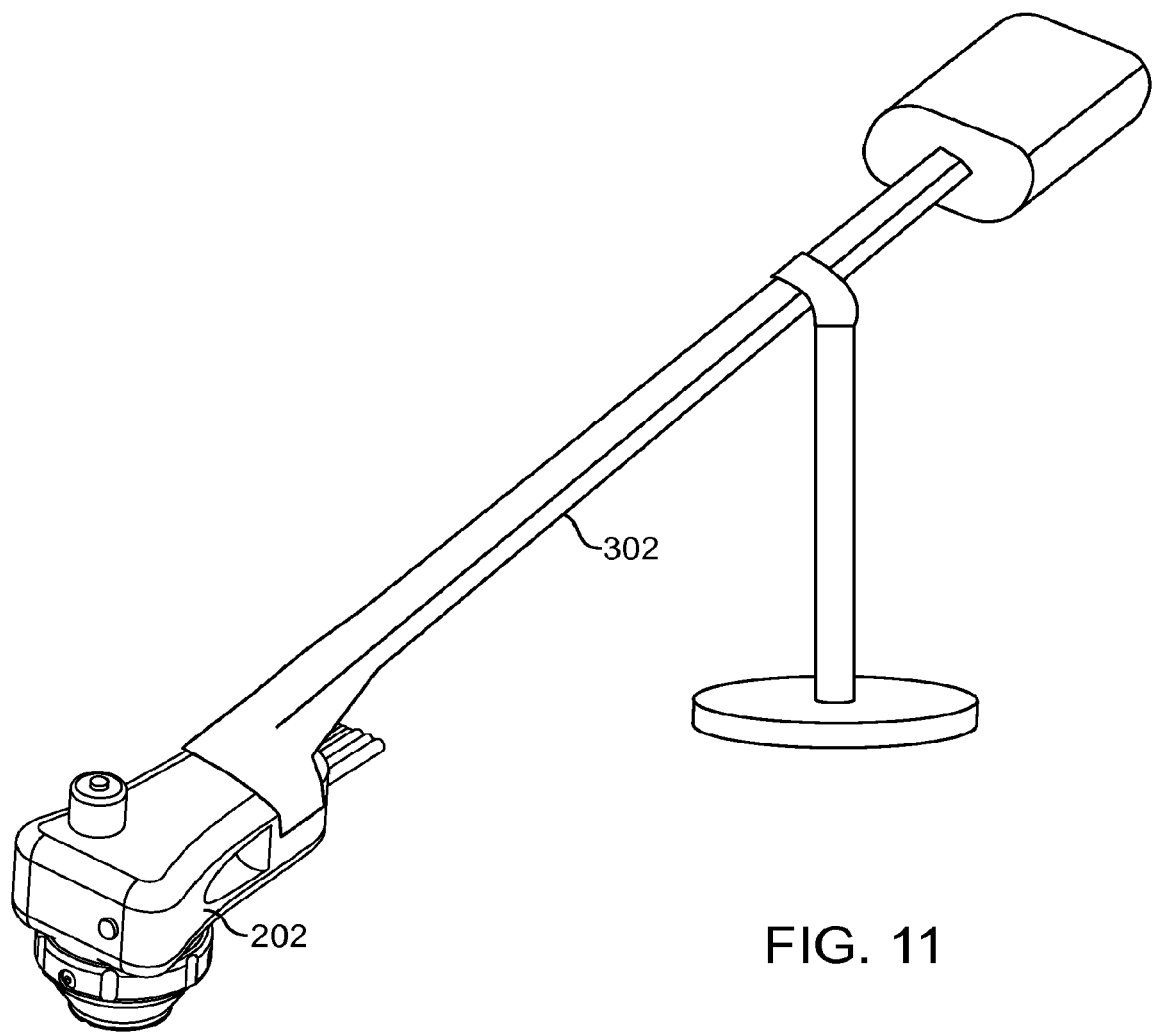
FIG. 11 shows a counterbalance arm for supporting a solution injection and insonation system according to the present invention.

The microbubble generator 106 may be mounted on (integrated with) the fluid injection device 202 thereby minimizing the distance that the solution travels before being injected into the tissue. The liquid reservoir 102 and gas reservoir 104 (if provided) may be removably connected to the micro bubble generator 106 as needed to generate microbubble solution. The injection device 202 may be manually supported by the operator. Alternatively, the injection device 202 may be supported on an arm 302 (FIG. 11) which may include a counterbalance to facilitate manipulation of the injection device 202.

Figure 12A:
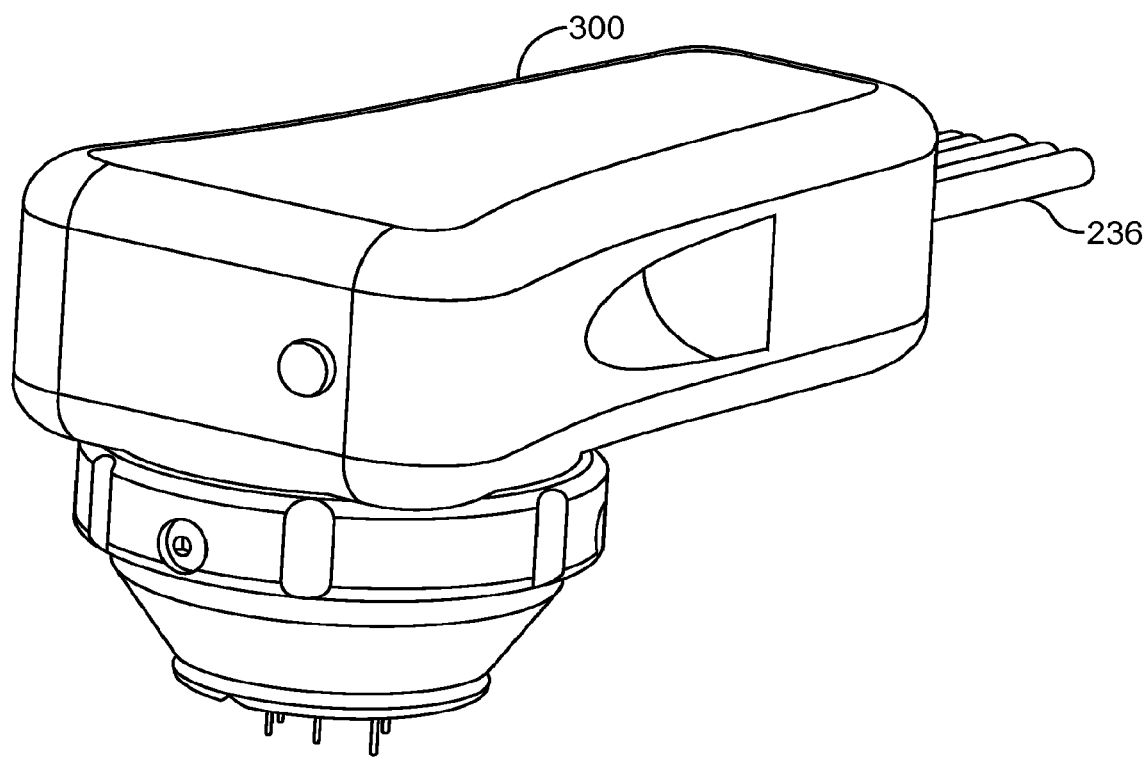
FIGS. 12A and 12B show a handpiece including a fluid injection mechanism used as part of a solution injection and insonation system of the present invention.

FIG. 12A depicts a handpiece 300 which includes fluid injection device 202 and which is coupled to the microbubble generator 106 (not illustrated) by a flexible conduit 236. This design minimizes the size and weight of handpiece 300 being handled by the operator since the handpiece 300 does not include the micro bubble generator 106.

Figure 12B:
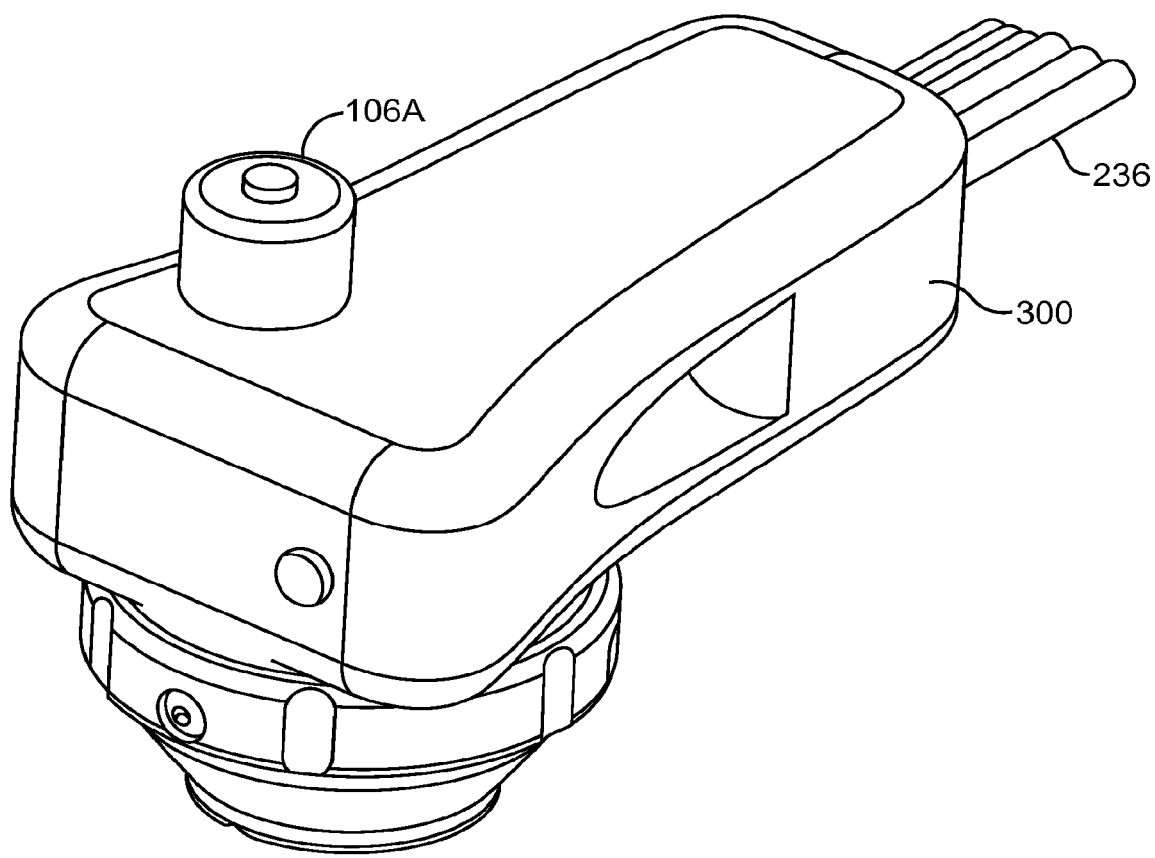

FIG. 12B depicts a handpiece 300 using the cartridge 106A mounted on the fluid injection device 202. This embodiment minimizes the distance that the microbubble solution travels before being injected into the tissue.

According to one embodiment the system of the invention includes a container which may be an enclosed or sealed cartridge 106A or it may be an open container. If the container is sealed it includes a measured amount of a solution. Obviously, if the container is not sealed then solution may be freely added as needed.

The system includes a needle array including at least one needle. The needle array 214 being in fluid connection with the container.

The solution includes any of the solutions disclosed herein. The solution includes a liquid. The solution may further include a gas which may be partially or fully dissolved within the solution.

The container may be enclosed and the solution may be maintained at greater than atmospheric pressure.

The needle array 214 includes at least one needle 218 which may be any of the needles disclosed herein.

The aforementioned gas may include one or more gases selected from the group of air, oxygen, carbon dioxide, carbon dioxide, perfluoropropane, argon, hydrogen, Halothane, Desflurane, Sevoflurane, Isoflurane, and Enflurane.

The solution may include one or more of a vasoconstrictor, a surfactant, and an anesthetic. Moreover, the vasoconstrictor may include one or more of Norepinephrine, Epinephrine, Angiotensin II, Vasopressin and Endothelin.

Optionally, the system may include refrigeration means for maintaining the container at a predefined temperature range. Moreover, the container may be thermally insulated.

The system may further include an ultrasound transducer apparatus 204 for transmitting ultrasound waves to the tissue. Preferably, the transducer apparatus 204 is operated in synchronism with the injection of solution into the tissue.

The transducer apparatus 204 may transmit ultrasound energy at a first setting to facilitate the distribution, absorption and/or uptake of solution by the tissue, i.e., sonoporation.

Ultrasound parameters that enhance the distribution of the solution include those conditions which create microstreaming, such as large duty cycle pulsed ultrasound (>10% duty cycle) or continuous wave ultrasound at a range of frequencies from 500 kHz to 15 MHz, focused or unfocused, and a mechanical index less than 4. According to one embodiment the mechanical index (MI) falls within the range $0.5 \leq MI \leq 4$. According to another embodiment the mechanical index falls within the range $0.5 \leq MI \leq 1.9$.

Sonoporation leading to increased absorption and/or uptake of the solution in the tissue can be generated by pulsed wave or continuous wave ultrasound, at a range of frequencies from 500 kHz to 15 MHz, focused or unfocused and medium to high mechanical index (MI>1.0). The preferred embodiment is pulsed wave ultrasound at a frequency of 500 kHz, unfocused, with high mechanical index (MI>1.9) in order to reproducibly create pores that are temporary or longer lasting pores.

The transducer apparatus 204 may transmit ultrasound energy at a second setting to facilitate the generation of bubbles by bringing dissolved gas out of solution, i.e., stable cavitation.

Ultrasound parameters for stable cavitation such as large duty cycle pulsed ultrasound (>10% duty cycle) or continuous wave ultrasound at a range of frequencies from 2 MHz to 15 MHz, focused or unfocused, and a mechanical index (MI) $0.05 \leq MI \leq 2.0$.

The transducer apparatus 204 may transmit ultrasound energy at a third setting to facilitate transient cavitation, i.e., popping bubbles.

Ultrasound parameters for transient cavitation at a range of frequencies from 500 kHz to 2 MHz, focused or unfocused, and a mechanical index (MI) greater than 1.9. The duty cycle required for transient cavitation may be very low, and the preferred embodiment is a wideband pulse (1 to 20 cycles) transmitted at a duty cycle less than 5%.

The transducer apparatus 204 may include any of the transducers disclosed herein, and may be operably connected to the needle array 214.

The transducer apparatus 204 may transmit ultrasound energy at a fourth frequency range to facilitate the pushing of bubbles within the tissue by acoustic streaming and/or acoustic radiation force. Ultrasound Acoustic Streaming and Radiation Force Sound propagating through a medium produces a force on particles suspended in the medium, and also upon the medium itself. Ultrasound produces a radiation force that is exerted upon objects in a medium with an acoustic impedance different than that of the medium. An example is a nanoparticle in blood, although, as one of ordinary skill will recognize, ultrasound radiation forces also may be generated on non-liquid core carrier particles. When the medium is a liquid, the fluid translation resulting from application of ultrasound is called acoustic streaming.

The ability of radiation force to concentrate microbubbles in-vitro and in-vivo has been demonstrated, e.g., Dayton, et al., Ultrasound in Med. & Biol., 25(8):1195-1201 (1999). An ultrasound transducer pulsing at 5 MHz center frequency, 10 kHz pulse repetition frequency ("PRF"), and 800 kPa peak pressure, has been shown to concentrate microbubbles against a vessel wall in-vivo, and reduce the velocity of these flowing agents an order of magnitude. In addition, the application of radiation to concentrate drug delivery carrier particles and the combined effects of radiation force-induced concentration and carrier fragmentation has been demonstrated. See U.S. patent application Ser. No. 10/928,648, entitled "Ultrasonic Concentration of Drug Delivery Capsules," filed Aug. 26, 2004 by Paul Dayton et al., which is incorporated herein by reference.

Acoustic streaming and optionally radiation force may be used to "push" or concentrate microbubbles injected into the tissue along a cell membrane. Notably, acoustic streaming has previously been used to push or concentrate carrier particles within a blood vessel. In contrast, the present invention utilizes acoustic streaming to push bubbles within subcutaneous tissue to concentrate the bubble against the walls of cells to be treated.

According to one aspect of the present invention, a solution containing microbubbles is injected into subcutaneous tissue or a solution containing dissolved gas is injected into subcutaneous tissue and insonated to bring the gas out of solution thereby generating bubbles within the subcutaneous tissue. The bubbles are pushed against the cell walls using acoustic streaming, and then insonated to induce transient cavitation to enhance the transport of the solution through the cell membrane and/or mechanically disrupt the cell membrane to selectively lyse cells.

The ultrasound parameters useful for inducing acoustic streaming include ultrasound waves having center frequencies about 0.1-20 MHz, at an acoustic pressure about 100 kPa-20 MPa, a long cycle length (e.g., about >10 cycles and continuous-wave) OR a short cycle length (e.g., about <10 cycle), and high pulse repetition frequency (e.g., about >500 Hz). The specific parameters will depend on the choice of carrier particle, as detailed further below, and can be readily determined by one of ordinary skill in the art.

According to one embodiment, the transducer apparatus 204 includes a single transducer capable of operating a plurality of operating modes to facilitate stable cavitation, transient cavitation, acoustic streaming, and sonoporation. According to another embodiment, the transducer apparatus 204 includes first and second transducers with first transducer optimized for popping bubbles (transient cavitation) and the second transducer optimized for bringing dissolved gas out of solution (stable cavitation) and/or pushing the bubbles using acoustic radiation force.

The transducer apparatus may produce focused, unfocused, or defocused ultrasound waves. Focused ultrasound refers to generally converging ultrasound waves, unfocused ultrasound refers to generally parallel ultrasound waves and defocused ultrasound wave refers to generally diverging ultrasound waves.

However, according to a preferred embodiment, the transducer apparatus 204 selectively produces unfocused and/or defocused ultrasound waves. For example, it may be desirable to utilize unfocused waves during transient cavitation, and defocused waves during stable cavitation. To this end the transducer apparatus may include a flat transducer, i.e., a transducer having a generally planar acoustic wear layer (acoustic window) for producing unfocused ultrasound waves (nonconverging waves) and/or a convex transducer, i.e., a transducer having a convex acoustic wear layer for producing defocused ultrasound waves (diverging waves).

Figure 14:
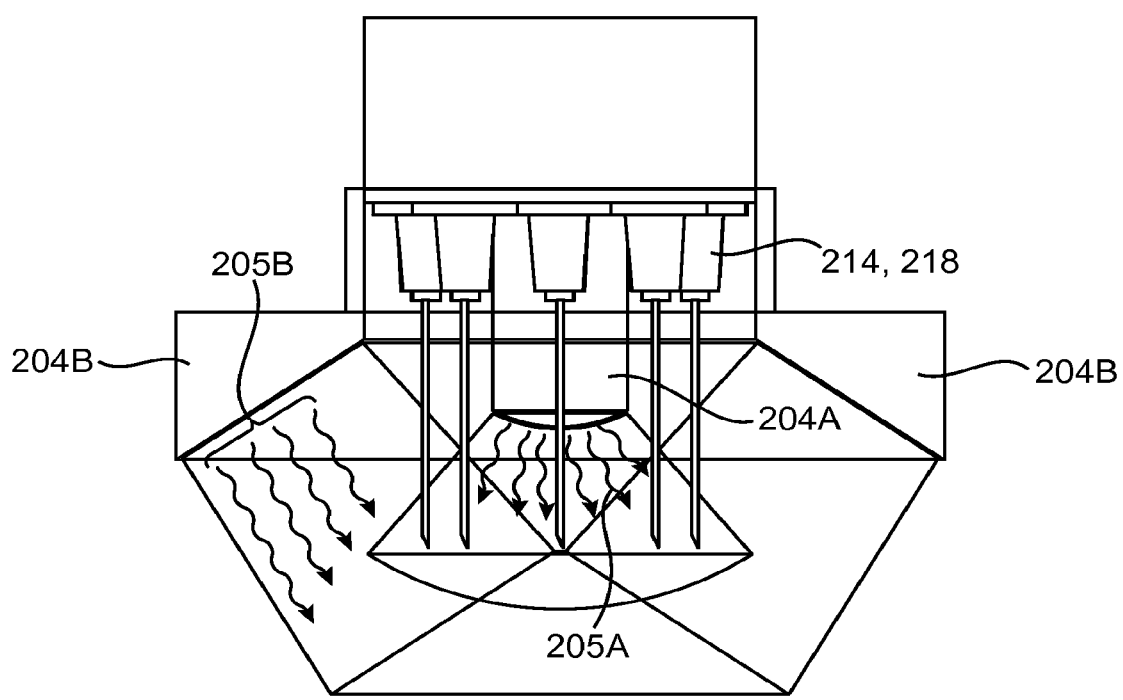
FIG. 14 is a section view of a transducer apparatus according to the present invention.

As will be appreciated by one of ordinary skill in the art, there are many different configurations for the ultrasound apparatus. FIG. 14 depicts an embodiment in which the transducer apparatus 204 includes an inner transducer 204A and an outer transducer 204B. In the illustrated embodiment, the inner transducer 204A has a convex shaped acoustic wear layer for producing defocused waves 205A, and the outer transducer 204B has a planar shaped acoustic wear layer for producing unfocused waves 205B. However, both of the inner and outer transducers 204A and 204B may be planar or both may be convex. Still further, one or both of the inner and outer transducers may be concave, i.e., may have a concave acoustic wear layer for producing focused waves. Thus, the ultrasound apparatus 204 may include any combination of focused, unfocused, and defocused transducers.

The inner and outer transducers depicted in FIG. 14 are both circular and the outer transducer surrounds (encircles) the inner transducer. However, other configurations are contemplated and fall within the scope of the invention. According to a presently preferred embodiment, the inner transducer is used to produce stable cavitation and the outer transducer is used to create transient cavitation. However, the relative positions may be swapped with the inner transducer producing transient cavitation and the outer transducer producing stable cavitation.

The ultrasound apparatus 204 illustrated in FIG. 14 includes a needle array 214 of the type described elsewhere in this disclosure. The transducer apparatus 204 of FIG. 14 may be incorporated in any of the embodiments disclosed herein which include an ultrasound transducer. Notably, the transducer apparatus 204 may be incorporated in system 200.

It should be noted that the transducer apparatus 204 may include one or more arrays of transducers. For example, the transducer apparatus may include an array of transducers for stable cavitation and/or an array of transducers for transient cavitation.

According to another aspect of the present invention, a solution which may or may not include microbubbles is injected into subcutaneous tissue. The solution is pushed against the cell walls using acoustic streaming, and then the subcutaneous tissue is insonated to induce sonoporation and facilitate the uptake/absorption of solution by the tissue. Solution is injected an insonated using a system such as system 200 depicted in FIG. 13 which does not include a bubble generator 100. Absorption of the solution preferably results in cell lysis.

As described in U.S. Utility patent application Ser. No. 11/292,950 filed Dec. 2, 2005, the ultrasound energy from ultrasound generator 206 is applied to the tissue 220 via ultrasound transducer 204. Ultrasound control unit 208 controls the various ultrasound parameters and generally controls the supply of ultrasound by generator 206. Preferably, ultrasound control unit 208 communicates with the injection control unit 210 to synchronize the application or ultrasound energy with the injection of fluid. It may for example be desirable to quickly apply energy to the tissue before the microbubbles dissipate or are absorbed by the tissue.

The ultrasound transducer 204 is preferably configured to deliver unfocused ultrasound at an intensity and pressure sufficient to noninvasively cavitate the micro bubbles within tissue thereby causing cell lysis. The intensity and pressure of the ultrasound applied to the tissue is preferably selected to minimize the heating of tissue and in particular avoid burning the patient's skin. The transducer 204 may include a thermocouple 238 or the like to monitor the temperature of the transducer 204.

In at least one embodiment the liposculpture system 200 (FIG. 2) includes an ID reader 250 (shown in dashed lines), and the needle array 214 includes an identifier 252 (shown in dashed lines), which uniquely identifies the needle array 214. The ID reader 250 reads the identifier 252, and preferably authenticates or verifies the needle array 214. The identifier 252 may contain information identifying the characteristics of the needle array 214 such as length and gauge of needles. The identifier 252 may further include identifying information which may be used to track the number of injection cycles (needle deployments) or use time for a given array 214.

The reader 250 preferably communicates with the injection control unit 210. The injection control unit 210 may count the number of injection cycles that a given needle array 214 has been used, and may warn the operator if the number exceeds a threshold number. The injection control unit 250 may use information stored on the identifier 252 to adjust the injection depth or injection flow rate. The injection control unit 210 may further inhibit usage of a needle array if it cannot authenticate, verify or read the identifier 252.

The identifier 252 may be a barcode label, a radio frequency tag, smart chip or other machine-readable medium such as known in the art.

The ultrasound transducer 204 may also include an identifier 252. The identifier 252 may be used to store information identifying the characteristics of the transducer 204, which is used by the ultrasound control unit 208 in setting or verifying the treatment settings. The ultrasound control unit 208 may inhibit insonation if it cannot authenticate, verify or read the identifier 252.

As described above, the transducer 204 may be integrated with the needle array 214 in which case a single identifier 252 may store information describing characteristics of both the needle(s) 218 and the transducer 204. The ultrasound control unit 208 may use information on the identifier 252 to track the amount of time the identified ultrasound transducer 204 has been operated and at what power levels, and may inhibit insonation if the accumulated insonation time exceeds a threshold value.

The constituent components of the device 100 may be formed of any sterilizable, biocompatible material. Moreover, some or all of the components may be disposable, i.e., manufactured for single-patient use, to minimize potential cross-contamination of patients. The needle array 214 is preferably a disposable component, as the needles 218 will likely dull with use.

One or more optical or pressure sensors 254 (FIG. 5) may be provided to measure pressure exerted on the handpiece 300 (FIG. 12A) when the handpiece is placed in abutment with the tissue. The pressure sensor(s) 254 may provide a safety interlock function to prevent inadvertent deployment of the needle array 214 and/or actuation of the transducer 204 unless pressure is detected as the handpiece 300 is placed in abutment with the tissue. If two or more pressure sensors 254 are provided the injection of solution and/or insonation may be inhibited unless each of the measured pressure values fall within a predefined window and/or so long as the difference between any given two measured pressure values is less than a threshold value. The pressure sensor(s) 254 may, for example, be provided on the needle array 214 (FIG. 4) or on the fluid injection device 202 (not illustrated). Alternatively, other sensing means, possibly optical or capacitive, may be used to detect proper positioning of the needle array against the tissue to be treated.

It may be advantageous to couple the needles 218 with the ultrasound transducer 204 such that ultrasound is transmitted through the needle(s) 218 to the tissue. Applying ultrasound in this manner may facilitate targeted cavitation and/or may facilitate penetration of the needle(s) 218 into the tissue.

Figure 13:
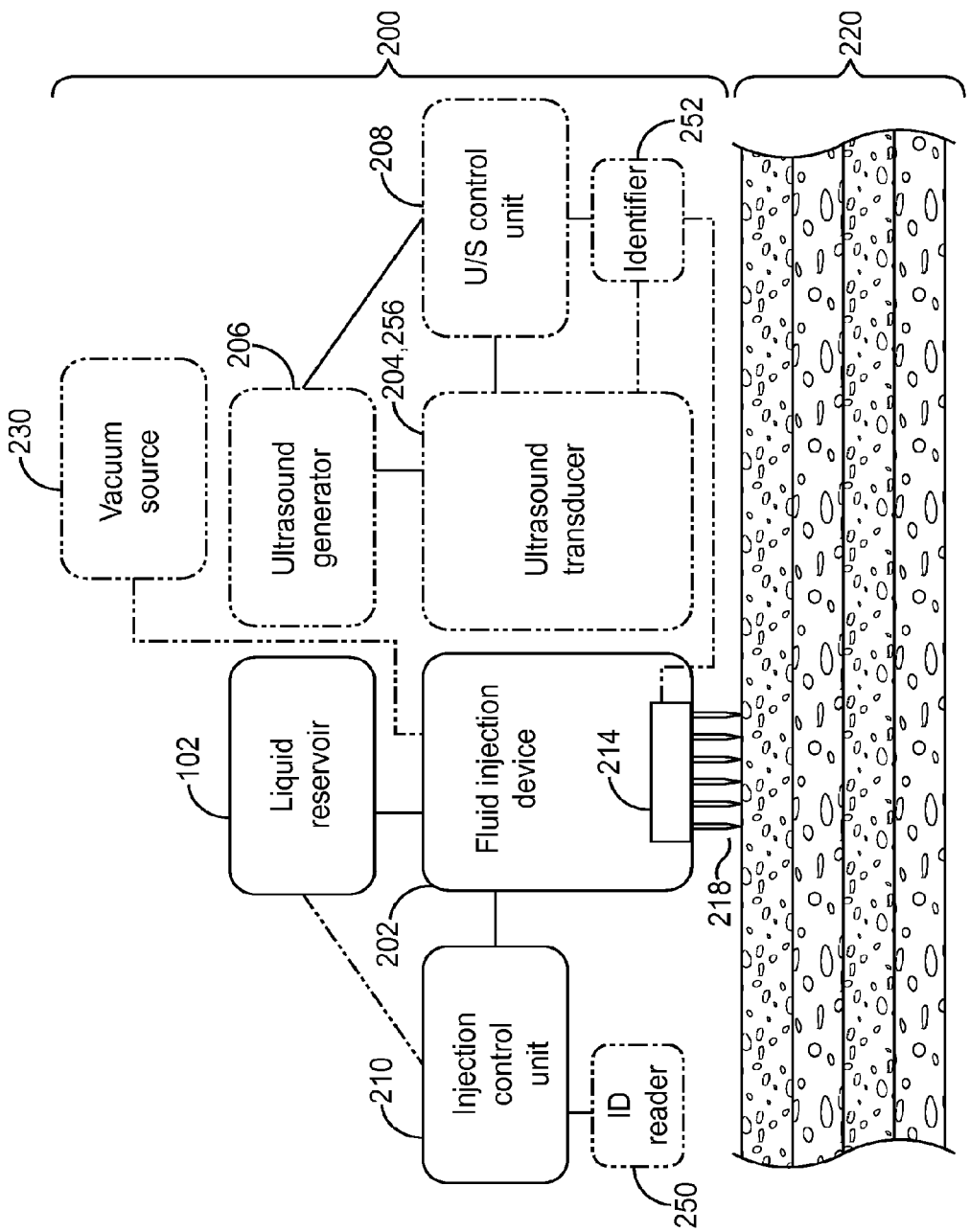
FIG. 13 is a block diagram of an alternate embodiment of the tissue cavitation system which does not utilize a bubble generator.

FIG. 13 is a block diagram of a system 200 for a fat lysing system according to the present invention. The system 200 is identical to the system 200 of FIG. 2 but excludes the bubble generator 100. Moreover, the ultrasound transducer 204, ultrasound generator 206, and ultrasound control unit 208 are shown in dashed lines to indicate that these are optional components. The system 500 may be used to inject a fat lysing solution (as will be described below in greater detail) with or without the use of ultrasound.

According to one embodiment, the fat lysing solution includes epinephrine as its active ingredient. The epinephrine may be combined with an aqueous solution, isotonic saline, normal saline, hypotonic saline, hypotonic solution, or a hypertonic solution. The solution may optionally include one or more additives/agents to raise the pH (e.g., sodium bicarbonate) or a buffering agent such those listed in Table 5 above or other buffering agents such as known in the art.

According to a presently preferred embodiment the fat lysing solution includes epinephrine in hypotonic buffered saline.

The inclusion of ultrasound in system 200 may facilitate the absorption and/or distribution of the fat lysing solution. The inclusion of ultrasound in system 200 may facilitate the absorption and/or distribution of the fat lysing solution. More particularly, the ultrasound may be used to enhance the distribution, absorption, and/or uptake of the solution in the tissue by permanently or temporarily opening pores in the cell membrane (sonoporation), generating microstreaming in the solution, or locally heating the solution or the tissue. According to one aspect of the invention, the ultrasound generator 206 may be operated at a first setting to facilitate distribution of the solution and then it may be operated at a second setting to facilitate absorption. The sonoporation may be reversible or irreversible.

The system 200 may include an optional ultrasound transducer 258 for vibrating the needles 218 to facilitate tissue penetration and/or a needle rotation mechanism 256 which may be used in conjunction with side-firing needles 218 to facilitate even distribution of the solution. The same transducer apparatus 204 used to facilitate absorption and/or distribution of the solution may be used to facilitate tissue penetration thereby eliminating the need for a separate transducer 258.

The system 200 may include any or all of the features described in this disclosure including means for selectively adjusting the amount of solution injected by each of the needles 218 and/or the rate or pressure at which the solution is injected into the tissue. Still further the system 200 may include the selective adjustment of the injection depth and/or the tissue apposition mechanism as described above. Mode of Operation/Method of Use According to a first mode of operation, solution is percutaneously injected into subcutaneous tissue, and the tissue is insonated at a first ultrasound setting to distribute the solution. Once the solution has been distributed the tissue is insonated at a second setting to induce sonoporation thereby inducing cell lysis. According to this mode of operation the solution need not contain microbubbles as they do not contribute to cell lysis. To increase the efficacy of this mode of operation it is recommended to repeat the injection and insonation of the tissue through 10 to 50 cycles.

According to a second mode of operation, a solution containing microbubbles is percutaneously injected into subcutaneous tissue, and the tissue is insonated at a first ultrasound setting to distribute the solution and/or push the microbubbles against the cell walls. Thereafter the tissue is insonated at a second setting (for between 1 millisecond and 1 second) to induce transient cavitation inducing cell lysis. To increase the efficacy of this mode of operation it is recommended to repeat the injection and insonation of the tissue through 10 to 50 cycles.

It should be appreciated that it is important to synchronize the timing of the insonation. Notably, the microbubbles will be absorbed by the tissue and/or go into solution within a relatively short period of time. Thus, it is important to distribute the microbubbles (using acoustic radiation force) and induce transient cavitation within a relatively short time after the solution has been injected into the subcutaneous tissue.

According to a presently preferred embodiment, the tissue is insonated to facilitate distribution of the micro bubble solution through acoustic radiation force and/or microstreaming occurs simultaneously as the solution is injected into the tissue or within a very short amount of time afterward. The injection of a small amount of the microbubble solution takes approximately 200 milliseconds and insonation to induce distribution through acoustic radiation force takes between 1 millisecond and 1 second. Next, the tissue is insonated to induce transient cavitation for approximately 400 milliseconds.

According to a third mode of operation, a solution containing dissolved gas, i.e., dissolved gas bubbles is percutaneously injected into subcutaneous tissue, and the tissue is insonated at a first ultrasound setting to bring the bubbles out of solution (for between 100 microseconds and 1 millisecond) followed immediately by insonation at a second setting (for between 1 millisecond and 1 second) to distribute the solution and/or push the microbubbles against the cell walls. Thereafter the tissue is insonated at a third setting (for between 100 microseconds and 1 second) to induce transient cavitation inducing cell lysis. To increase the efficacy of this mode of operation it is recommended to repeat the injection and insonation of the tissue through 10 to 50 cycles.

It should be appreciated that it is important to synchronize the timing of the insonation. Notably, the microbubbles will be absorbed by the tissue and/or go into solution within a relatively short period of time. Thus, it is important to distribute the microbubbles (using acoustic radiation force) and induce transient cavitation within a relatively short time after the bubbles have been brought out of solution.

According to a presently preferred embodiment, the tissue is insonated to induce stable cavitation and bring the bubbles out of solution after the solution has been injected into the subcutaneous tissue. Satisfactory stable cavitation results have been achieved by insonating for approximately 100 microseconds. Thereafter the tissue is insonated to facilitate distribution of the micro bubble solution through acoustic radiation force and/or microstreaming occurs. Insonating for between 1 millisecond and 1 second is required to distribute the microbubbles. Immediately thereafter the tissue is insonated to induce transient cavitation for approximately 400 milliseconds.

The invention may be combined with other methods or apparatus for treating tissues. For example, the invention may also include use of skin tightening procedures, for example, ThermaCool™ available from Thermage Corporation located in Hayward, Calif., Cutera Titan™ available from Cutera, Inc. located in Brisbane, Calif., or Aluma™ available from Lumenis, Inc. located in Santa Clara, Calif.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

We claim:

1. A system for the generation and delivery of microbubbles, comprising:
   a liquid reservoir configured to contain a fluid;
   a gas reservoir configured to contain a gas or vapor;
   a bubble generator,
      wherein the bubble generator is in fluidic communication with the liquid reservoir and the gas reservoir,
      wherein the bubble generator is configured to receive liquid from the liquid reservoir and gas from the gas reservoir and combine the received liquid and gas to create a solution comprising microbubbles;
   a fluid injection device,
      wherein the fluid injection device comprises a needle array comprising one or more needles; and
      wherein the fluid injection device is in fluidic communication with the bubble generator and is configured to receive the solution comprising microbubbles and to inject the solution comprising microbubbles into a region of target tissue.

2. The system of claim 1, further comprising, a fluid metering device configured to control the amount of fluid dispensed from the liquid reservoir to the bubble generator.

3. The system of claim 1, further comprising, a gas metering device configured to control the amount of gas or vapor dispensed from the gas reservoir to the bubble generator.

4. The system of claim 1, wherein the needle array comprises a plurality of needles, wherein the system further comprising a needle deployment mechanism, wherein the needle deployment mechanism deploys the needles of the needle array from a first position to a desired injection depth, wherein the desired injection depth is optionally adjustable to depths between 6 mm and 10 mm below the dermis.

5. The system of claim 1, wherein the needle array is configured to inject the solution comprising microbubbles at a plurality of injection depths in the target tissue.

6. The system of claim 1, wherein the needle array comprises a plurality of needles having a first length, and wherein the needle array can be removed from the fluid injection device and replaced with a different needle array comprising a plurality of needles having a second length.

7. The system of claim 1, wherein the one or more needles of the needle array each comprise a single injection orifice linearly aligned with a shaft of the one or more needles.

8. The system of claim 1, wherein the one or more needles of the needle array each comprise one or more side-firing orifices positions orthogonally to a shaft of the one or more needles.

9. The system of claim 1, wherein the microbubble generator comprises a rotor, a blade, a paddle, a whisk, or a semipermeable membrane to generate the microbubbles.

10. The system of claim 1, wherein the microbubble generator is configured to generate a solution containing microbubbles that is biocompatible by adjusting one or more of the ratio of gas to liquid in the solution, the size of the microbubbles and the biocompatibility of the fluid and the gas or vapor.

11. A system for the generation and delivery of microbubbles, comprising:
- a gas source;
- a solution container comprising a solution;
- a solution agitator in fluidic communication with the solution container and the gas source,
  - wherein the solution agitator is configured to receive gas from the gas source and solution from the solution container and mix the gas and the solution to form a solution comprising microbubbles; and
- an injection member comprising at least one needle,
  - wherein the injection member is in fluidic communication with the solution agitator and is configured to receive the solution comprising microbubbles and to inject the solution comprising microbubbles into a region of target tissue.

12. The system of claim 11, wherein the solution agitator comprises a cartridge and the agitator agitates or shakes the cartridge to generate the microbubbles, and wherein the cartridge is configured to receive measured amounts of liquid and gas.

13. The system of claim 11, wherein the solution comprises hypotonic saline and the gas source comprises air.

14. The system of claim 11, further comprising a cooling element to maintain the solution comprising microbubbles at a pre-determined temperature to further enhance solubility/saturation of the gas in the solution.

15. The system of claim 14, wherein the filter element comprises a HEPA filter.

16. The system of claim 14, wherein the bubble generator is configured to be pressurized to enhance the saturation of the gas in the solution.

17. The system of claim 14, wherein the system further comprises a fluid pressurization mechanism configured to maintain the fluid at a desired pressurization.

18. The system of claim 14, further comprising a cooling element configured to maintain the solution comprising microbubbles at a pre-determined temperature to further enhance solubility/saturation of the gas in the solution.

19. The system of claim 14, further comprising at least one regulatory element configured to regulate one or more of the volume, pressure, and rate at which the solution comprising microbubbles is injected into the target tissue.

20. A system for the generation and delivery of microbubbles, comprising:
- a liquid reservoir configured to contain a fluid;
- a bubble generator;
- a filter element configured to filter a gas or vapor prior to the gas or vapor being passed to the bubble generator,
  - wherein the bubble generator is in fluidic communication with the liquid reservoir and the filter element,
  - wherein the bubble generator is configured to receive liquid from the liquid reservoir and gas or vapor filtered through the filter element and combine the received liquid and gas or vapor to create a solution comprising microbubbles;
- a fluid injection device,
  - wherein the fluid injection device comprises a needle array comprising one or more needles; and
  - wherein the fluid injection device is in fluidic communication with the bubble generator and is configured to receive the solution comprising microbubbles and to inject the solution comprising microbubbles into a region of target tissue.

* * * * *